US009980685B2

(12) United States Patent
Iwashita et al.

(10) Patent No.: US 9,980,685 B2
(45) Date of Patent: May 29, 2018

(54) RADIATION IMAGING APPARATUS AND CONTROL METHOD OF THE SAME

(71) Applicant: CANON KABUSHIKI KAISHA, Tokyo (JP)

(72) Inventors: Atsushi Iwashita, Saitama (JP); Toshio Kameshima, Kumagaya (JP); Tomoyuki Yagi, Honjo (JP); Katsuro Takenaka, Honjo (JP); Hideyuki Okada, Honjo (JP); Eriko Sato, Tokyo (JP); Takuya Ryu, Kokubunji (JP); Kosuke Terui, Honjo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days. days.

(21) Appl. No.: 15/643,681

(22) Filed: Jul. 7, 2017

(65) Prior Publication Data

US 2017/0303878 A1 Oct. 26, 2017

Related U.S. Application Data

(63) Continuation of application No. 14/675,852, filed on Apr. 1, 2015, now Pat. No. 9,737,271.

(30) Foreign Application Priority Data

| Apr. 9, 2014 | (JP) | 2014-080491 |
| May 7, 2014 | (JP) | 2014-096223 |
| Sep. 11, 2014 | (JP) | 2014-185696 |

(51) Int. Cl.
*A61B 6/00* (2006.01)
*G01T 1/24* (2006.01)
(Continued)

(52) U.S. Cl.
CPC .......... *A61B 6/4208* (2013.01); *A61B 6/4233* (2013.01); *A61B 6/5258* (2013.01);
(Continued)

(58) Field of Classification Search
CPC ... A61B 6/4208; A61B 6/4233; A61B 6/5258; A61B 6/542; H04N 5/32; H04N 5/3205; H04N 5/361
See application file for complete search history.

(56) References Cited

U.S. PATENT DOCUMENTS

| 7,408,167 B2 | 8/2008 | Kameshima et al. ... 250/370.09 |
| 7,421,063 B2 | 9/2008 | Takenaka et al. ............ 378/116 |

(Continued)

FOREIGN PATENT DOCUMENTS

| JP | H07-250283 | 9/1995 |
| JP | 2002-199278 | 7/2002 |

(Continued)

*Primary Examiner* — Eliza Osenbaugh-Stewart
(74) *Attorney, Agent, or Firm* — Fitzpatrick Cella Harper and Scinto

(57) ABSTRACT

A radiation imaging apparatus comprising a plurality of sensors arrayed to form a plurality of rows and a plurality of columns on a substrate and a driving unit configured to drive the plurality of sensors row by row, wherein the driving unit performs a first operation of driving the plurality of sensors while selecting the plurality of rows in a first order, and a second operation of driving the plurality of sensors while selecting the plurality of rows in a second order different from the first order after the first operation, such that a time difference is produced between a sensor in each row and a sensor in a neighboring row from the selection in the first order to the selection in the second order.

14 Claims, 25 Drawing Sheets

(51) Int. Cl.
*H04N 5/32* (2006.01)
*H04N 5/361* (2011.01)

(52) U.S. Cl.
CPC .............. *A61B 6/542* (2013.01); *H04N 5/32* (2013.01); *H04N 5/3205* (2013.01); *H04N 5/361* (2013.01)

(56) References Cited

U.S. PATENT DOCUMENTS

| | | | |
|---|---|---|---|
| 7,442,939 B2 | 10/2008 | Yagi et al. | 250/370.11 |
| 7,514,663 B2 | 4/2009 | Yagi et al. | 250/208.1 |
| 7,514,690 B2 | 4/2009 | Endo et al. | 250/370.14 |
| 7,564,038 B2 | 7/2009 | Endo et al. | 250/370.01 |
| 7,732,776 B2 | 6/2010 | Takenaka et al. | 250/370.01 |
| 7,839,977 B2 | 11/2010 | Kameshima et al. | 378/116 |
| 8,785,876 B2 | 7/2014 | Tajima | |
| 8,809,795 B2 | 8/2014 | Takenaka et al. | 250/370.08 |
| 2005/0078793 A1 | 4/2005 | Ikeda | 378/98.8 |
| 2008/0246065 A1 | 10/2008 | Takenaka et al. | 257/292 |
| 2010/0148080 A1 | 6/2010 | Endo et al. | 250/370.08 |
| 2010/0283875 A1 | 11/2010 | Naskali et al. | 348/243 |
| 2012/0212657 A1 | 8/2012 | Mo et al. | 348/300 |
| 2013/0083213 A1* | 4/2013 | Kawada | H04N 5/361 348/222.1 |
| 2013/0240712 A1 | 9/2013 | Takenaka et al. | 250/208.1 |
| 2013/0341525 A1 | 12/2013 | Maruta et al. | 250/394 |
| 2014/0061491 A1 | 3/2014 | Iwashita et al. | 250/393 |
| 2014/0112448 A1 | 4/2014 | Takenaka et al. | 378/114 |
| 2014/0241506 A1 | 8/2014 | Iwashita et al. | 378/91 |
| 2014/0361184 A1 | 12/2014 | Sato et al. | 250/370.08 |

FOREIGN PATENT DOCUMENTS

| | | |
|---|---|---|
| JP | 2003-190126 | 7/2003 |
| JP | 2008-259045 | 10/2008 |
| JP | 2013-258557 | 12/2013 |
| WO | 2011/152093 | 8/2011 |

\* cited by examiner

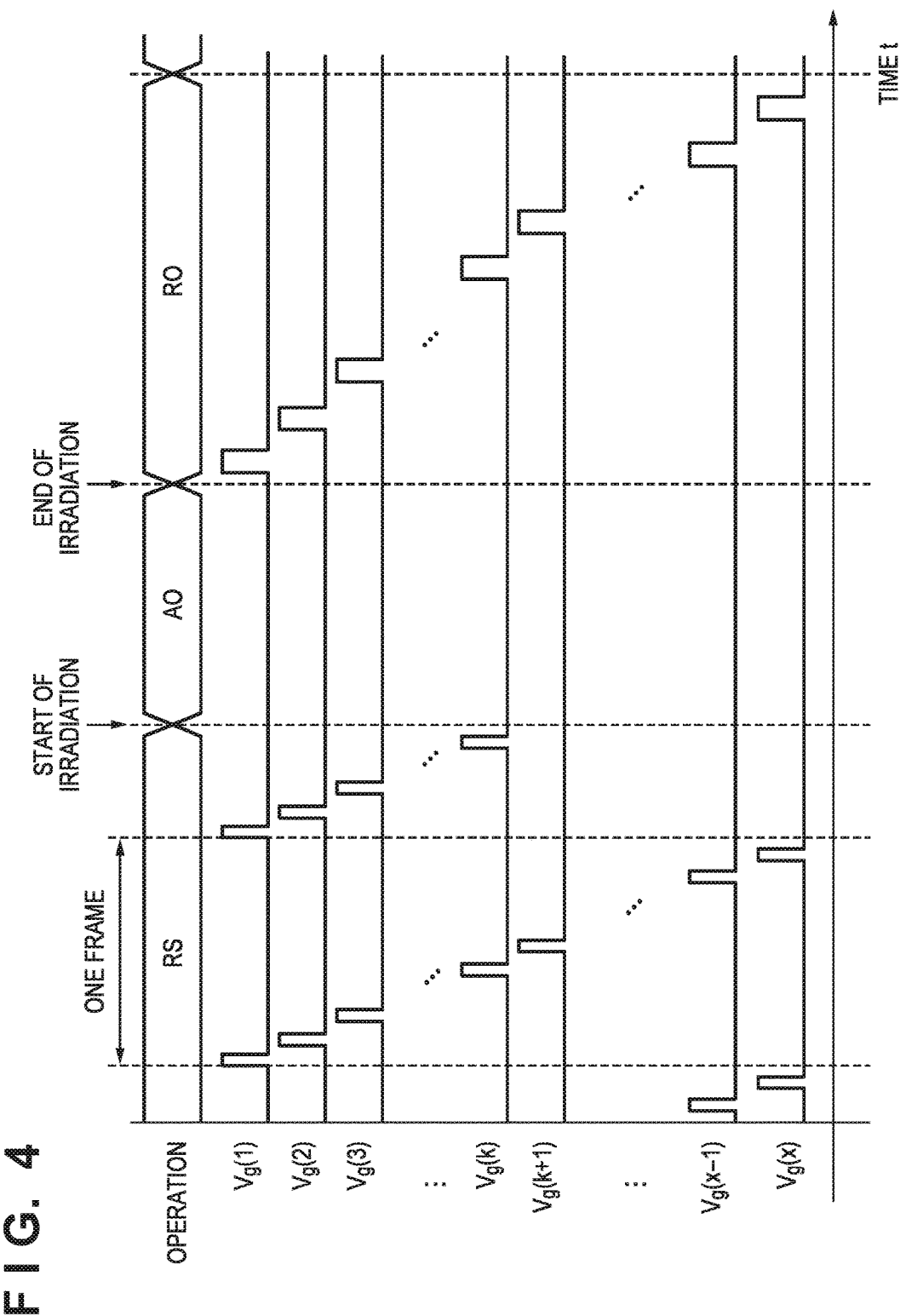

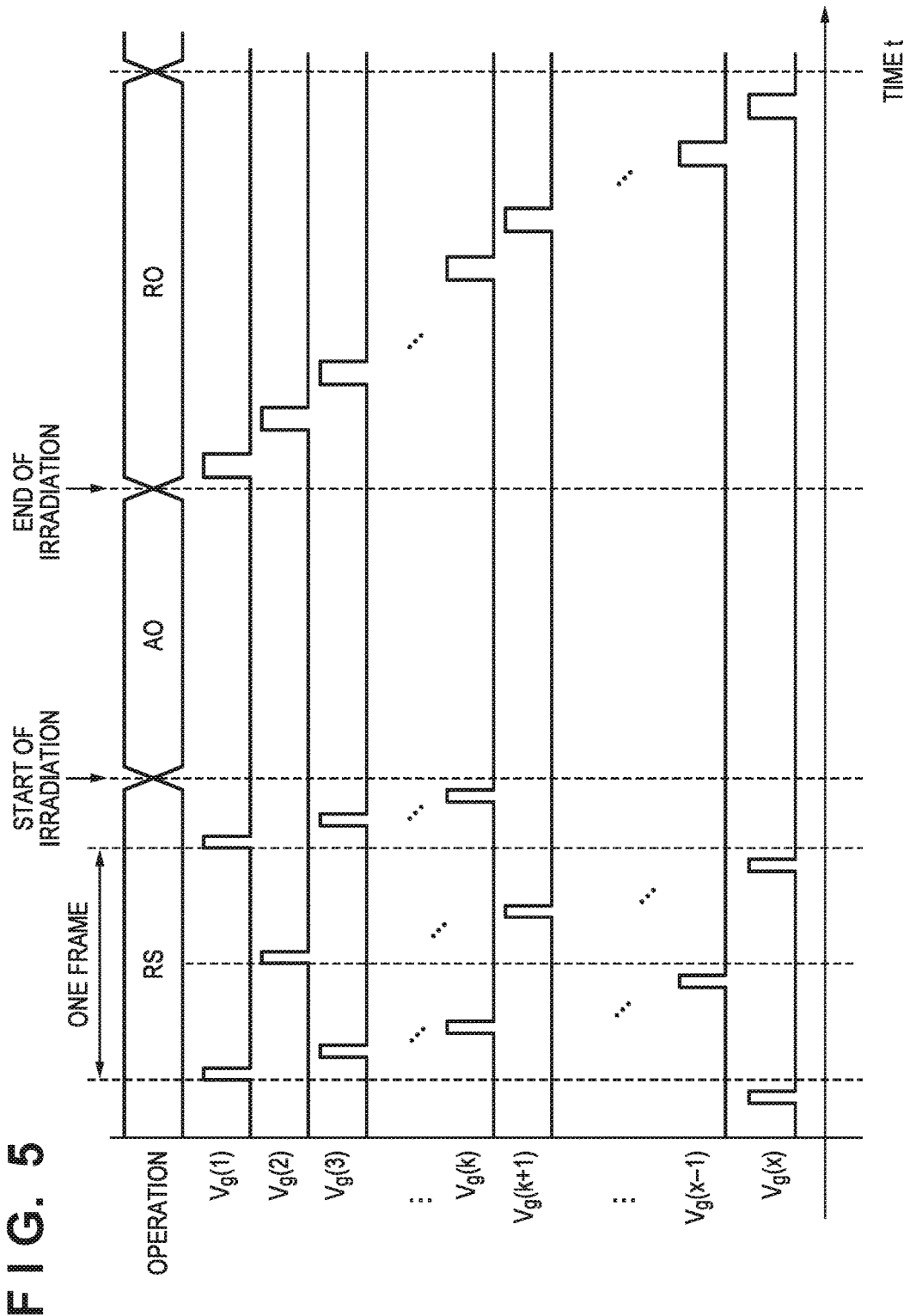

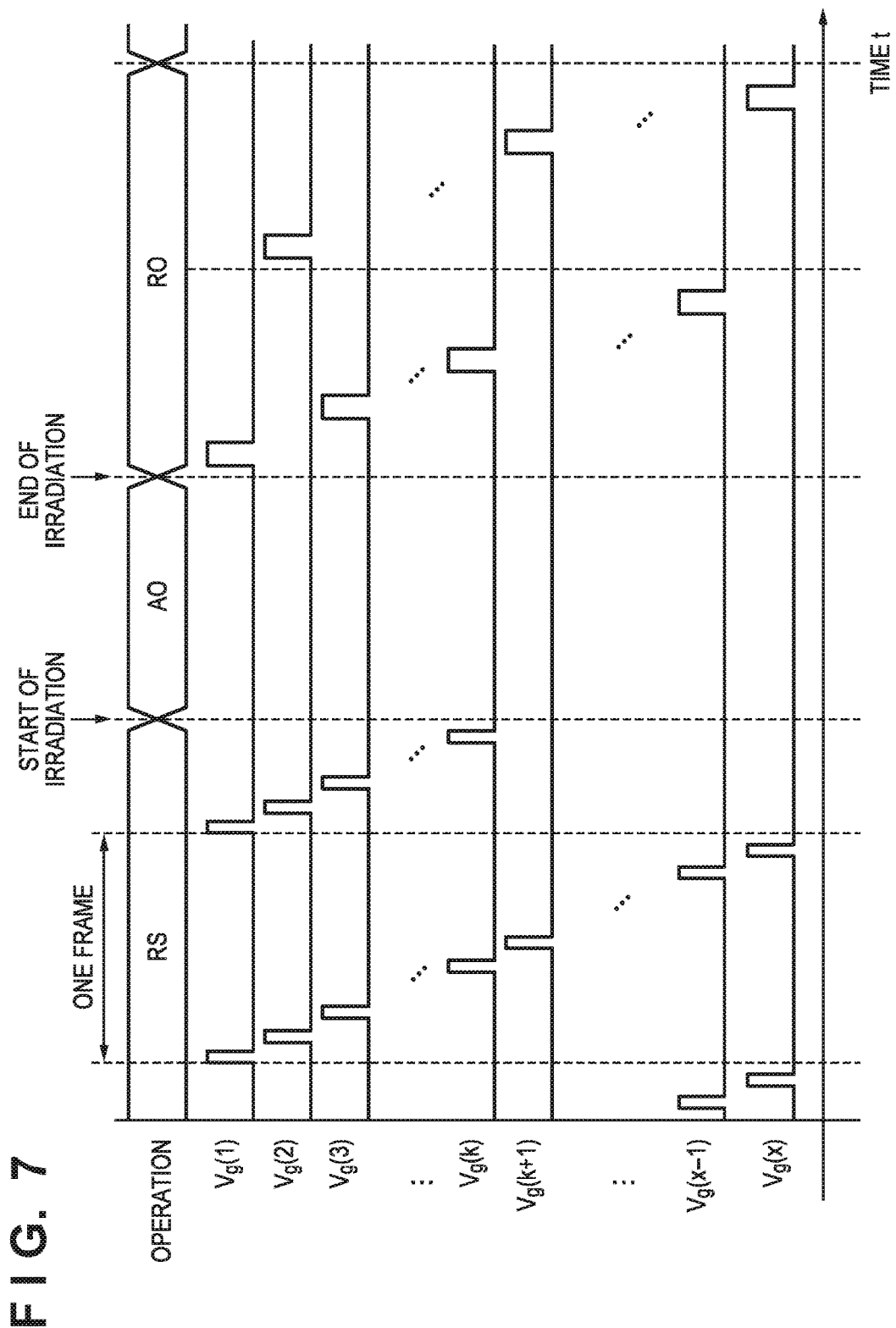

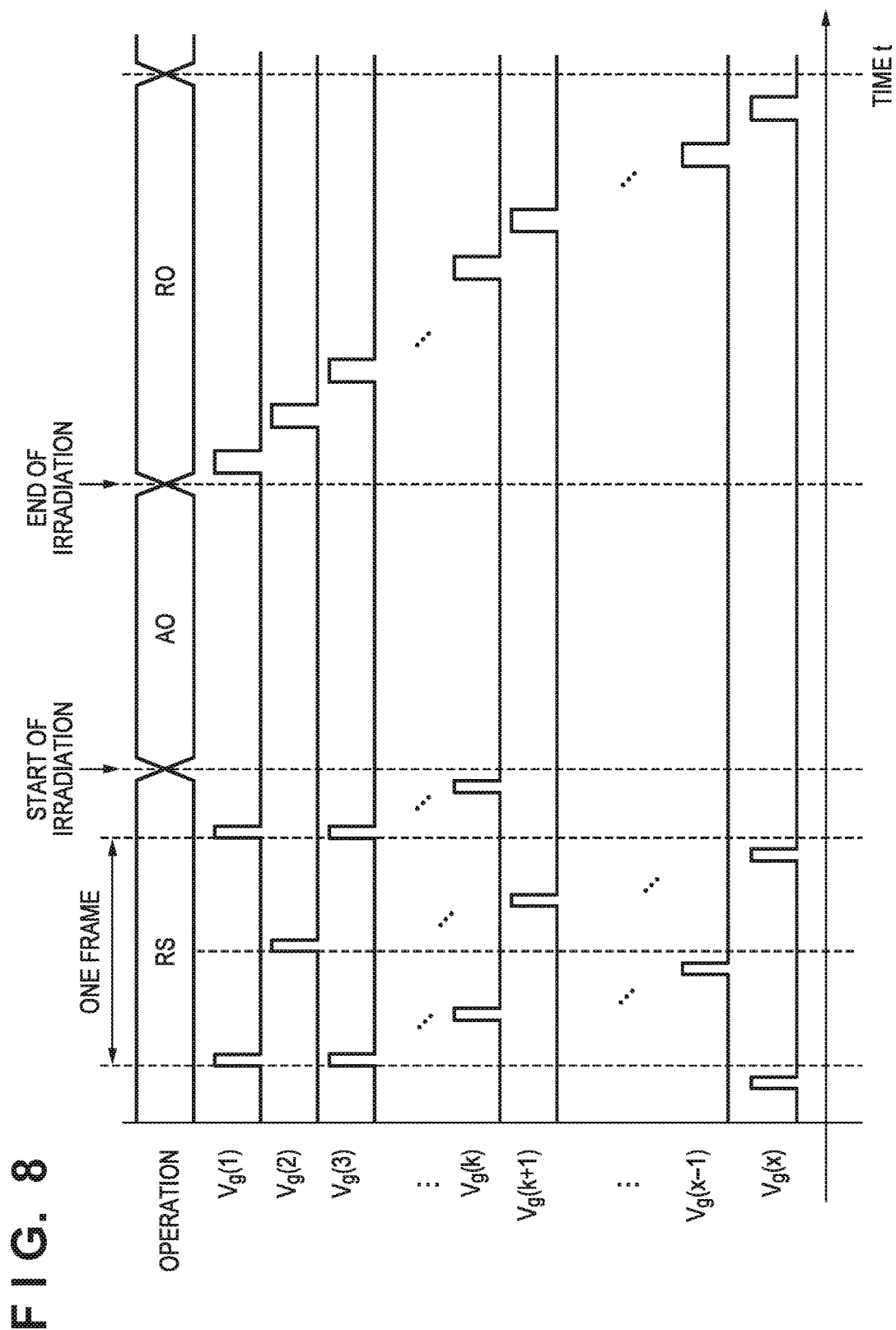

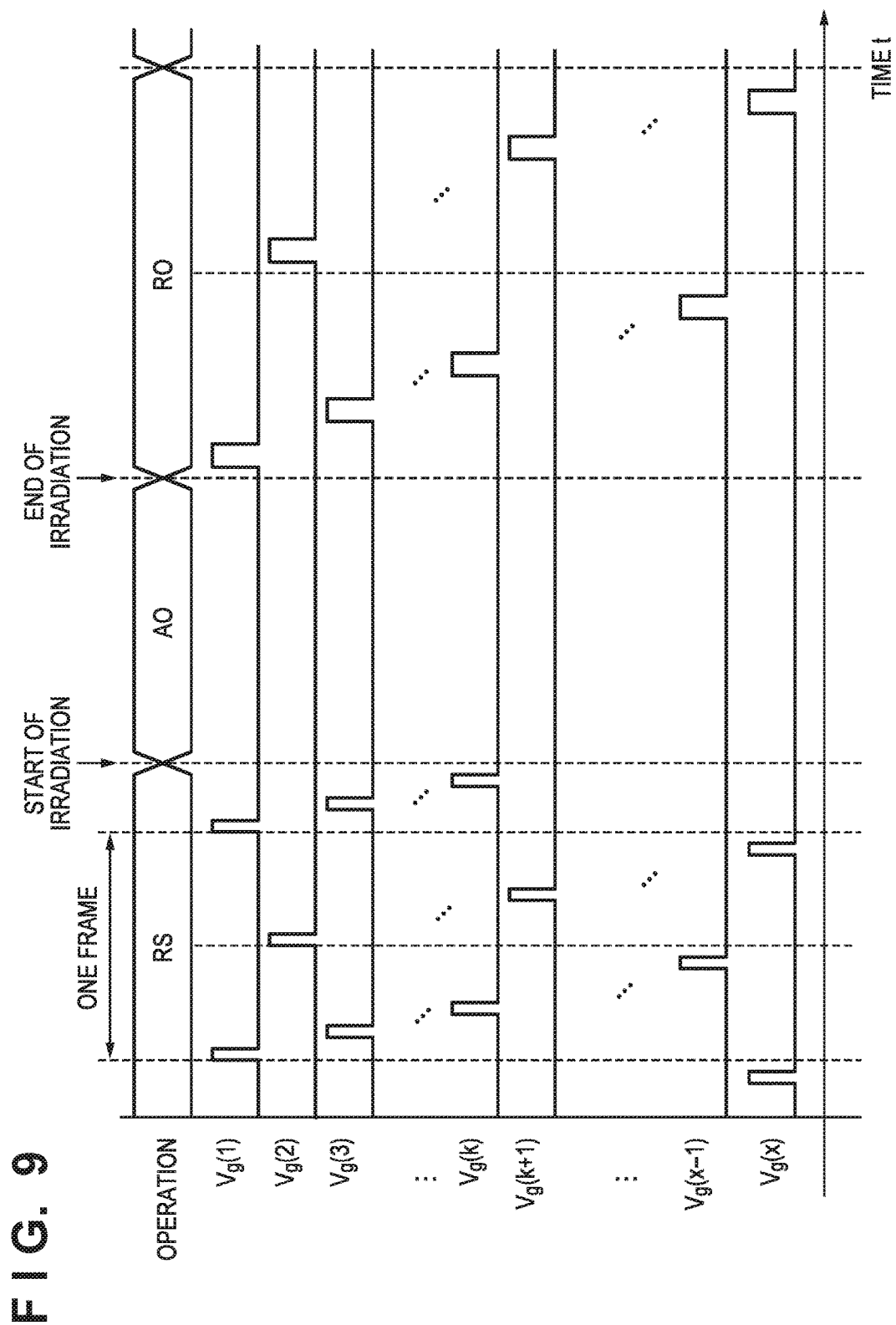

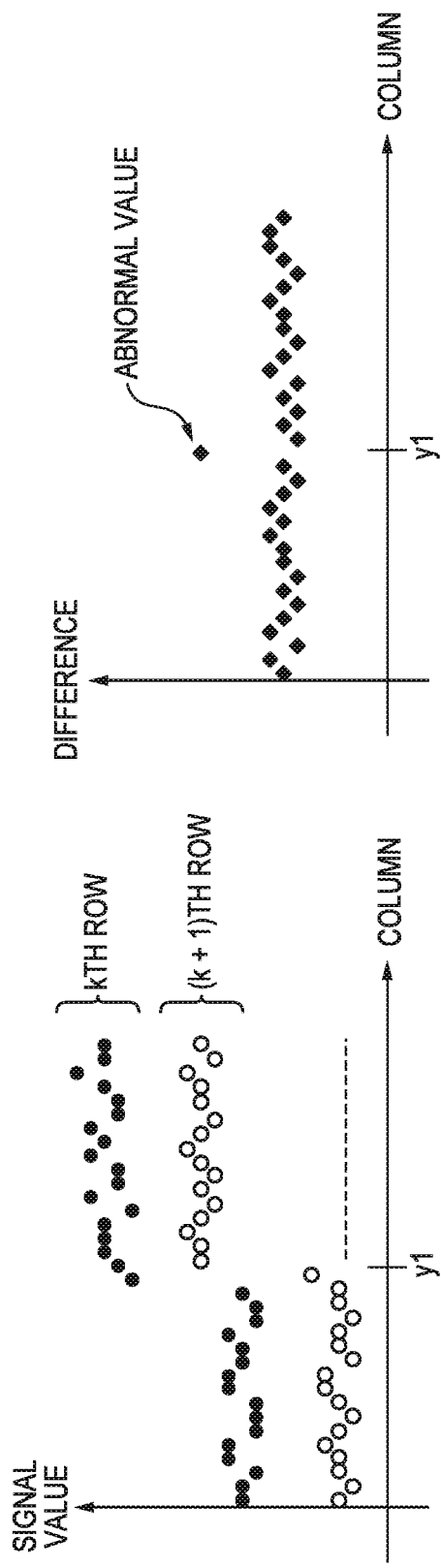

RADIATION IMAGING APPARATUS AND CONTROL METHOD OF THE SAME

RELATED APPLICATIONS

This application is a continuation of application Ser. No. 14/675,852, filed Apr. 1, 2015. It claims benefit of that application under 35 U.S.C. § 120, and claims benefit under 35 U.S.C. § 119 of Japanese Patent Application No. 2014-080491, filed Apr. 9, 2014, No. 2014-096223, filed May 7, 2014, and No. 2014-185696, filed Sep. 11, 2014. The entire contents of each of the mentioned prior applications are incorporated herein by reference.

BACKGROUND OF THE INVENTION

Field of the Invention

The present invention relates to a radiation imaging apparatus and a control method of the same.

Description of the Related Art

A radiation imaging apparatus includes a plurality of sensors arrayed on a substrate, and a driving unit for driving these sensors row by row. For example, in a still image sensing mode, after radiation is emitted to the radiation imaging apparatus and sensed by the sensors, the driving unit drives a sensor and reads out a signal (sensor signal) having a value corresponding to the radiation dose from the sensor. Also, in a moving image sensing mode or continuous imaging mode, for example, the above-mentioned radiation emission and sensor signal readout are repetitively performed.

Since the sensor signal contains a signal component and noise component corresponding to the radiation dose, correction for removing the noise component is performed on the sensor signal. Electric charge corresponding to noise such as a dark current is accumulated in a sensor with time, and the above-mentioned noise component contains a component corresponding to a time from the last driving of a sensor to the next driving of the sensor.

SUMMARY OF THE INVENTION

The present invention provides a technique advantageous in performing correction for removing a noise component from a sensor signal.

One of the aspects of the present invention provides a radiation imaging apparatus comprising a plurality of sensors arrayed to form a plurality of rows and a plurality of columns on a substrate and a driving unit configured to drive the plurality of sensors row by row, wherein the driving unit performs a first operation of driving the plurality of sensors while selecting the plurality of rows in a first order, and a second operation of driving the plurality of sensors while selecting the plurality of rows in a second order different from the first order after the first operation, such that a time difference is produced between a sensor in each row and a sensor in a neighboring row from the selection in the first order to the selection in the second order.

Further features of the present invention will become apparent from the following description of exemplary embodiments with reference to the attached drawings.

BRIEF DESCRIPTION OF THE DRAWINGS

FIG. 4 is a timing chart for explaining an example of an operation of the radiation imaging apparatus;

FIG. 5 is a timing chart for explaining an example of the operation of the radiation imaging apparatus;

FIG. 7 is a timing chart for explaining an example of the operation of the radiation imaging apparatus;

FIG. 8 is a timing chart for explaining an example of the operation of the radiation imaging apparatus;

FIG. 9 is a timing chart for explaining an example of the operation of the radiation imaging apparatus;

FIGS. 11A and 11B are views for explaining examples of a method of driving the radiation imaging apparatus;

FIGS. 12A and 12B are views for explaining examples of a signal value plot graph;

DESCRIPTION OF THE EMBODIMENTS (1. Arrangement Example of Radiation Imaging Apparatus)

Figure 1:
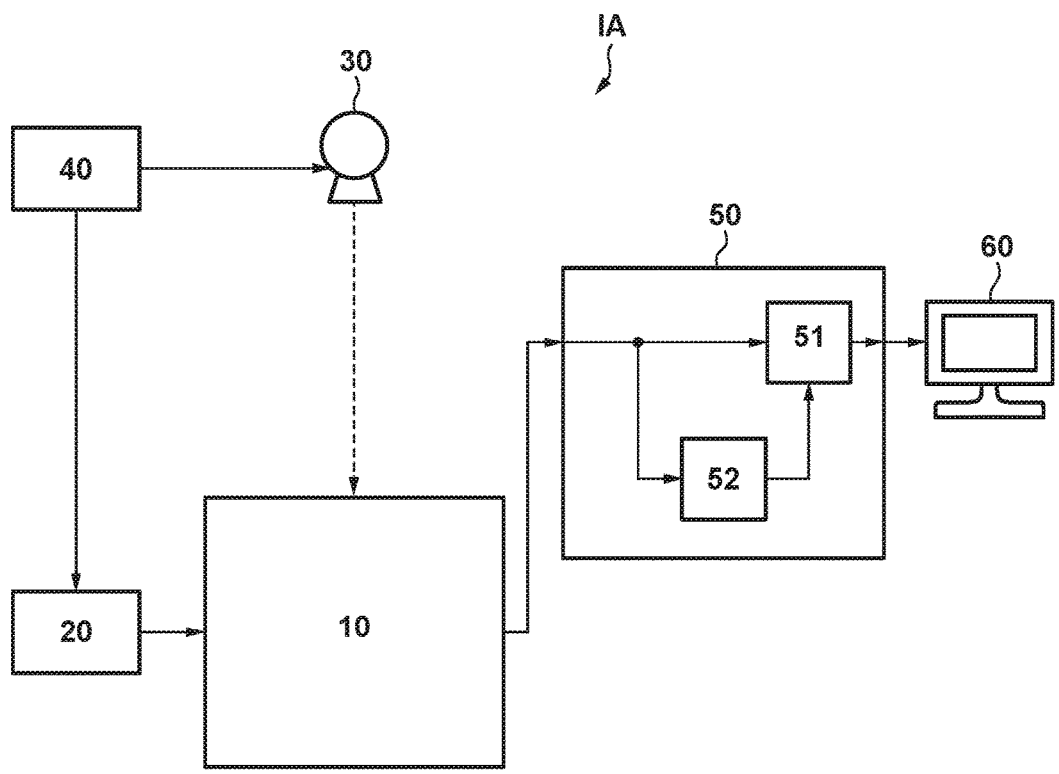
FIG. 1 is a view for explaining a system configuration example of a radiation imaging apparatus.

FIG. 1 is a block diagram showing an overall arrangement example of a radiation imaging apparatus or radiation inspection apparatus. In this example, an overall arrangement example of a radiation imaging apparatus IA (to be simply referred to as "an apparatus IA" hereinafter) will be described. The apparatus IA includes an imaging unit 10, driving unit 20, radiation generation source 30, control unit 40, processing unit 50, and display unit 60.

The imaging unit 10 has a sensor array in which a plurality of sensors for sensing radiation are arrayed. The imaging unit 10 may further include a scintillator (not shown) for converting radiation into light. In this case, a photoelectric conversion element for sensing converted light is used as each sensor. The imaging unit 10 having this arrangement detects radiation having passed through the body of a subject to be examined (for example, a patient), and obtains image data indicating information in the body of the subject to be examined.

Note that the imaging unit 10 can have a so-called indirect conversion type arrangement which converts radiation into light and then converts the light into an electrical signal as described above, but may also have a direct conversion type arrangement which (directly) converts radiation into an electrical signal.

The driving unit 20 drives the imaging unit 10 based on a predetermined driving signal or control signal, and performs driving control for performing radiation imaging. The radiation generation source 30 generates radiation based on a predetermined control signal, and irradiates the imaging unit 10. Note that the radiation includes an X-ray, $\alpha$-ray, $\beta$-ray, $\gamma$-ray, and the like. The control unit 40 outputs control signals to the driving unit 20 and radiation generation source 30, and controls the operations of the driving unit 20 and radiation generation source 30. The control unit 40 can also perform synchronous control on these units, thereby controlling the whole apparatus IA.

The apparatus IA can be configured such that the imaging unit 10 senses the start of irradiation. For example, the imaging unit 10 can be configured to sense the start of irradiation by using at least one or the other of the plurality of sensors. More specifically, the imaging unit 10 repetitively drives each sensor before irradiation, and senses the start of irradiation based on a signal from the sensor. Alternatively, the imaging unit 10 may also sense the start of irradiation based on a signal from a separately installed dedicated sensor. In this arrangement, synchronous control between the imaging unit 10 and other units can automatically be performed by, for example, the control unit 40.

The processing unit 50 receives image data from the imaging unit 10 and performs predetermined data processing. Also, the processing unit 50 includes a correcting unit 51 and calculating unit 52, and performs a correction process on the image data. The calculating unit 52 calculates correction information based on image data. The correcting unit 51 corrects the image data by using the calculated correction information. The display unit 60 receives image data from the processing unit 50 and displays an image (radiation image) showing the internal state of a subject to be examined.

Note that the apparatus IA is not limited to the above-described arrangement. For example, one unit may have a partial function of another unit, or two or more units may be integrated. For example, the imaging unit 10 may also include the control unit 40 and processing unit 50, or the control unit 40 and processing unit 50 may also be integrated. In addition, signal exchange between the individual units can be performed either wired or wireless communication.

Figure 2:
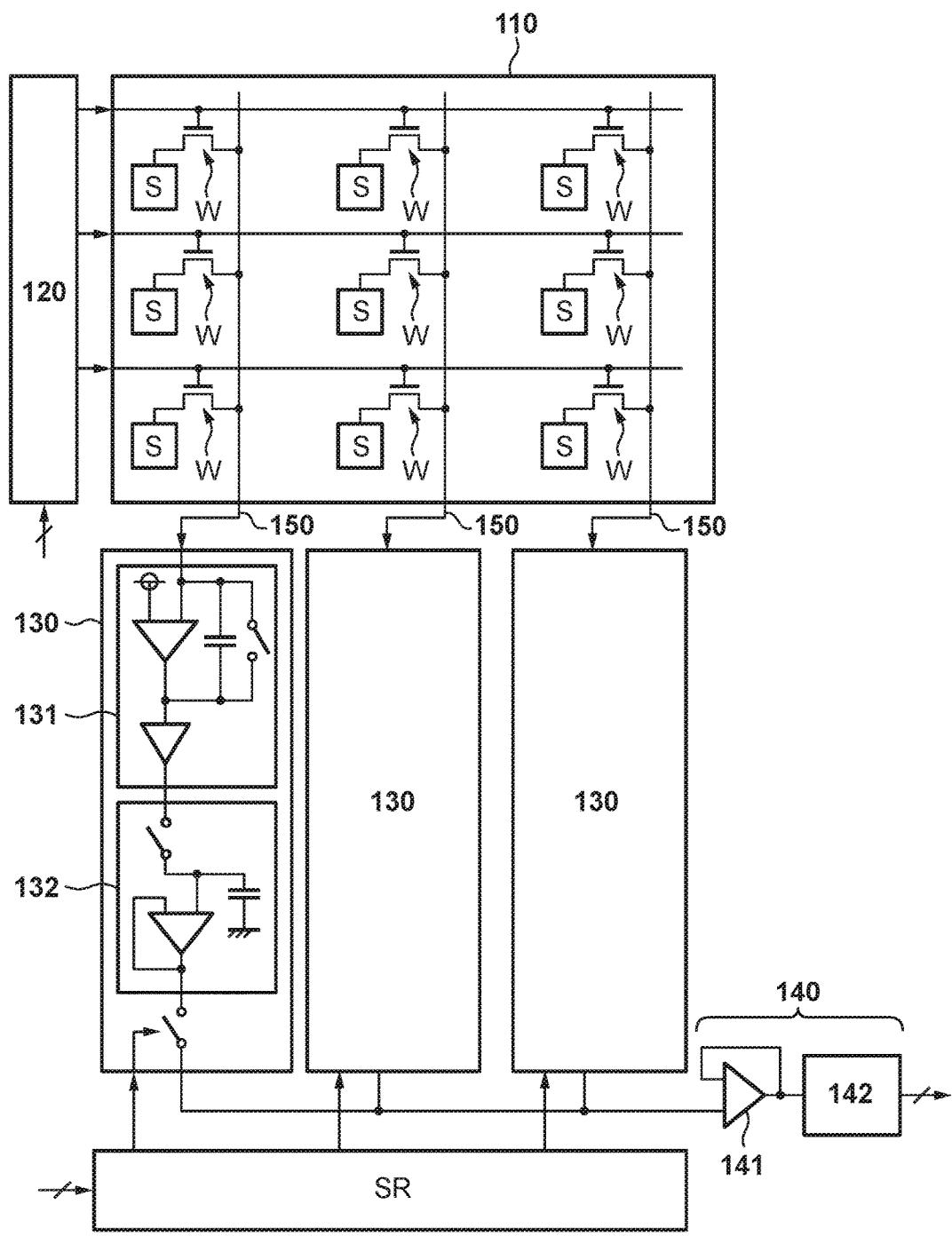
FIG. 2 is a view for explaining an arrangement example of an imaging unit.

FIG. 2 shows an arrangement example of the imaging unit 10. The imaging unit 10 includes, for example, a sensor array 110 in which a plurality of sensors S are arrayed, a sensor driving unit 120, signal readout units 130, and a signal output unit 140. Note that FIG. 2 exemplarily shows 3 rows×3 columns of the sensor array 110 in order to make the drawing easier to see.

The sensor driving unit 120 drives the sensors S row by row based on a signal from the driving unit 20, and causes each sensor S to output a signal corresponding to the amount of electric charge generated when the sensor senses radiation. The sensor driving unit 120 includes, for example, a shift register, and selects a row to be driven in order based on, for example, a clock signal.

For example, each of the plurality of sensors S includes a PIN photodiode or MIS photodiode, and is formed on a glass substrate by using amorphous silicon. Each sensor is connected to a switching element W for outputting a signal corresponding to the amount of electric charge generated by the sensor S. The signal is output to a column signal line 150 of a corresponding column by driving the switching element W. The switching element W is formed by, for example, a thin-film transistor (TFT).

The signal from the sensor S is also simply called "a sensor signal". In this example, one sensor S and a corresponding switching element W form a unit pixel, the sensor signal or a signal based on the sensor signal is also called "a pixel signal", and the value of this pixel signal is also called "a pixel value".

Each signal readout unit 130 includes, for example, a signal amplifier 131 for amplifying signals from the sensors S in each column, and a holding unit 132 for sampling and holding the amplified signals. For example, the held signals are sequentially read out based on a control signal from a shift register SR. The shift register SR supplies, to the signal readout unit 130, the control signal for reading out the signals held in the holding unit 132 based on, for example, a signal from the driving unit 20. In this arrangement, the signal readout unit 130 sequentially reads out signals from the sensors S in each column through the column signal line 150, and horizontally transfers the readout signals to the signal output unit 140.

The signal output unit 140 includes, for example, an output buffer amplifier 141 and A/D conversion unit 142. In this arrangement, the signal output unit 140 sequentially outputs signals read out by the signal readout unit 130 as image data (digital data) to the above-described processing unit 50.

(2. First Embodiment)

In the first embodiment, several examples of mainly a still image sensing mode will be explained.

(2-1. First Example)

Figure 3:
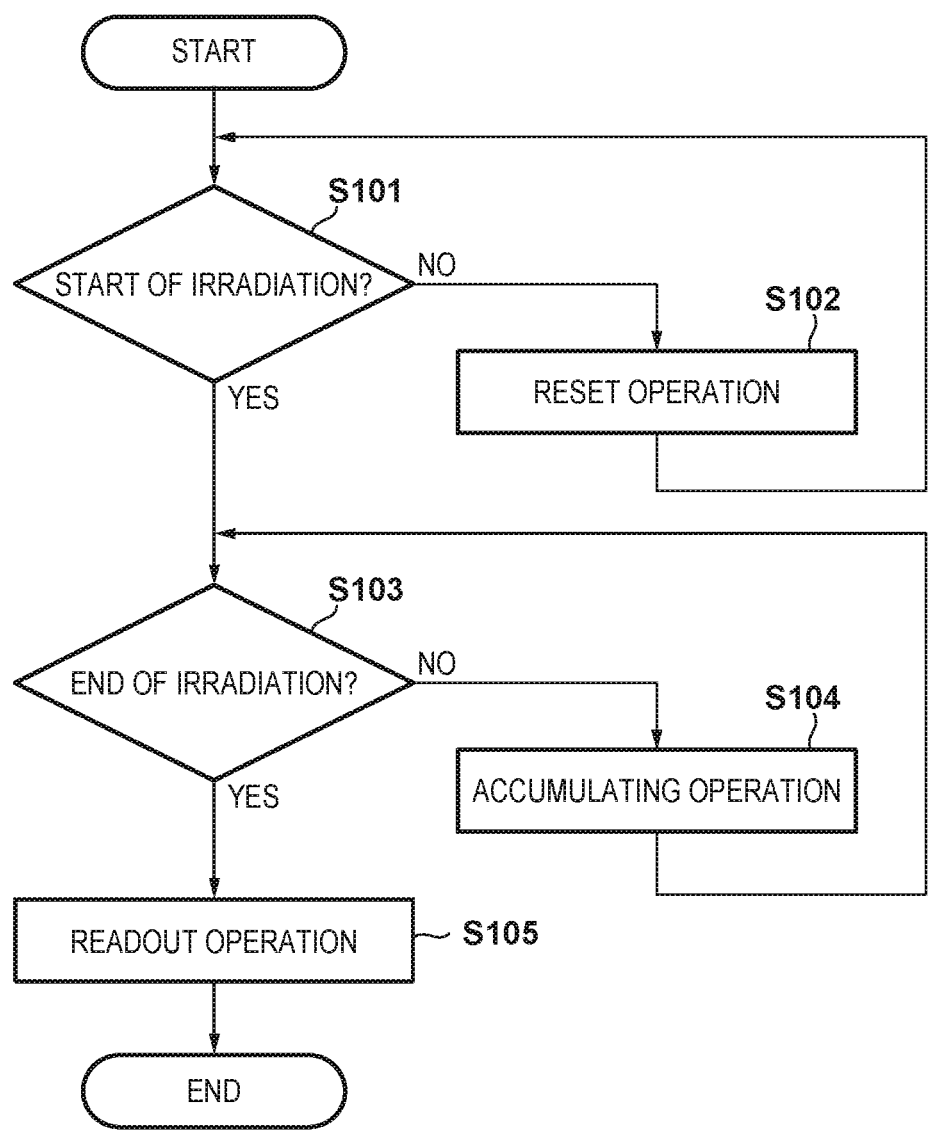
FIG. 3 is a flowchart for explaining an operation of the radiation imaging apparatus.

FIG. 3 shows a flowchart for performing radiation imaging. First, in step S101 (to be simply referred to as "S101" hereinafter, and this applies to other steps), whether irradiation is started is determined. If the irradiation is not started, the process advances to S102. If the irradiation is started, the process advances to S103.

In S102, a reset operation of initializing (resetting) the sensors S in the sensor array 110 is performed. This reset operation is repetitively performed until the irradiation is started in S101.

In S103, whether the irradiation is terminated is determined. If the irradiation is not terminated, the process advances to S104. If the irradiation is terminated, the process advances to S105.

In S104, an accumulating operation of accumulating electric charge in each sensor S is performed. In each sensor S, a corresponding switching element W is kept OFF, so electric charge whose amount corresponds to the emitted radiation dose is accumulated.

In S105, a readout operation of reading out a signal based on the amount of electric charge accumulated in each sensor S is performed. This readout operation may also be started in response to the elapse of a predetermined time from the start of irradiation.

That is, a reset operation of resetting each sensor S is repetitively performed before irradiation (S101 and S102). Then, the accumulating operation of accumulating electric charge in each sensor is performed in response to the start of irradiation (S103 and S104). After that, a signal is read out from each sensor S (S105).

Referring to FIG. 2 again, the above-mentioned reset operation is performed by, for example, turning on the switching element W while initializing (the feedback capacity of) the signal amplifier 130. Consequently, the electric charge generated in each sensor S due to noise such as a dark current before irradiation is equivalently released to a reference potential through the column signal line 150. On the other hand, the above-mentioned readout operation is performed by turning on the switching element W while keeping the signal amplifier 130 active. As a consequence, the electric charge generated in each sensor S by irradiation is read out as a signal through the column signal line 150.

In this specification, the above-mentioned reset operation, readout operation, and accumulating operation will respectively be referred to as "a reset operation RS", "a readout operation RO", and "an accumulating operation AO".

FIG. 4 shows, as the first reference example, a driving timing chart of the imaging unit 10 including the sensor array 110 having X rows x Y columns. The abscissa is the time axis. The ordinate indicates control signals $V_g(1)$ to $V_g(X)$ for driving the sensors S. For example, i is an arbitrary integer from 1 to X, and $V_g(i)$ is a control signal for driving each sensor S in the ith row. In this arrangement, $V_g(i)$ is a signal for controlling ON/OFF of a corresponding switching element W. The switching element W is turned on when $V_g(i)$ is at High level (H), and turned off when $V_g(i)$ is at Low level (L).

Before irradiation, the reset operation RS is repetitively performed. The reset operation RS is performed row by row in the order of the first row, the second row, . . . , the Xth row. After reset of the Xth row as the last row is completed, the reset operation RS is performed in order from the first row. FIG. 4 shows an example in which irradiation is started when resetting the kth row. In response to this, the reset operation RS is interrupted, and the accumulating operation AO is started. After that, the readout operation RO is started. Like the reset operation RS, the readout operation RO is performed row by row in the order of the first row, the second row, . . . , the Xth row.

Also, the pulse width of the control signal $V_g(i)$, which turns on the switching element W, is smaller in the reset operation RS than in the readout operation RO. Accordingly, the period of initialization of each sensor S is shortened in the reset operation RS, whereas a signal of each sensor S is properly read out in the readout operation RO.

Note that interrupting the reset operation RS is not essential, and the accumulating operation AO may also be started after reset of the Xth row as the last row is completed. For example, when the irradiation time is much longer than the time of one period of the reset operation RS (the time required for reset of the first to Xth rows), the accumulating operation AO may also be started after reset of the Xth row is completed.

FIG. 5 shows a driving timing chart of the imaging unit 10 according to the first example. This driving timing chart differs from the above-mentioned first reference example (FIG. 4) in the row driving order in the reset operation RS. In the above-mentioned first reference example, the reset operation RS is performed by a progressive method. On the other hand, the reset operation RS is performed by an interlace method in the first example.

More specifically, in the first example, after odd-numbered rows (the first row, the third row, the fifth row, . . . , the (X−1)th row) are reset, even-numbered rows (the second row, the fourth row, the sixth row, . . . , the Xth row) are reset. Note that FIG. 5 shows an example in which the kth row as a reset target when irradiation is started is an odd-numbered row.

Figure 6A:
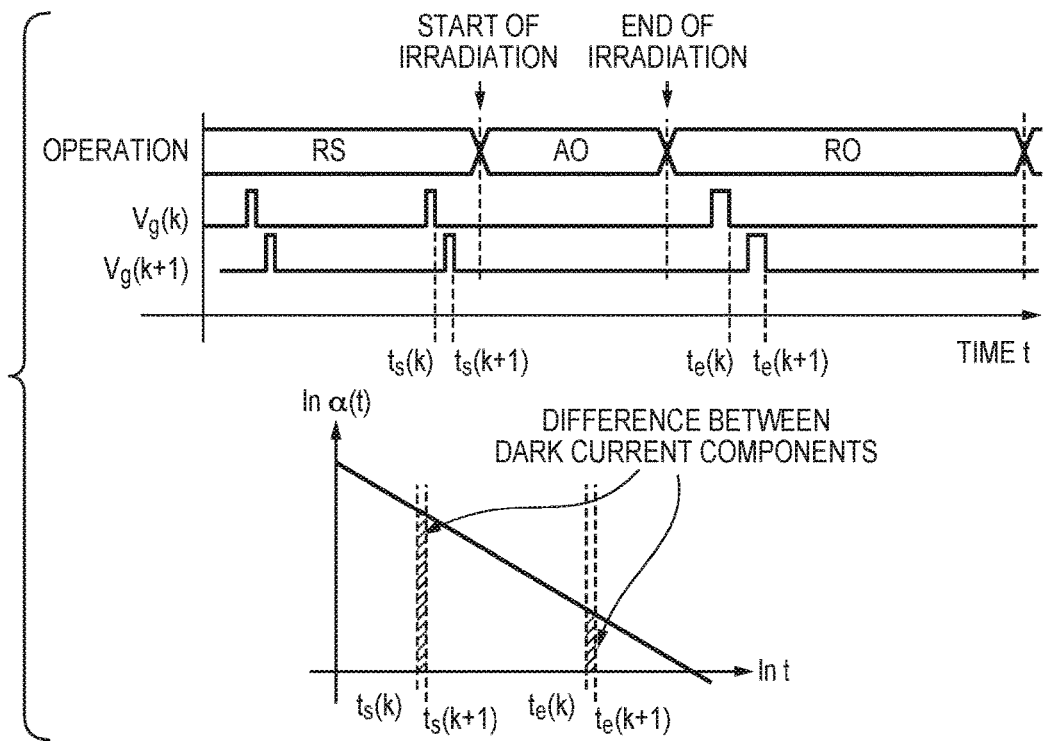
FIGS. 6A and 6B are timing charts for explaining a part of the operation of the radiation imaging apparatus.
Figure 6B:
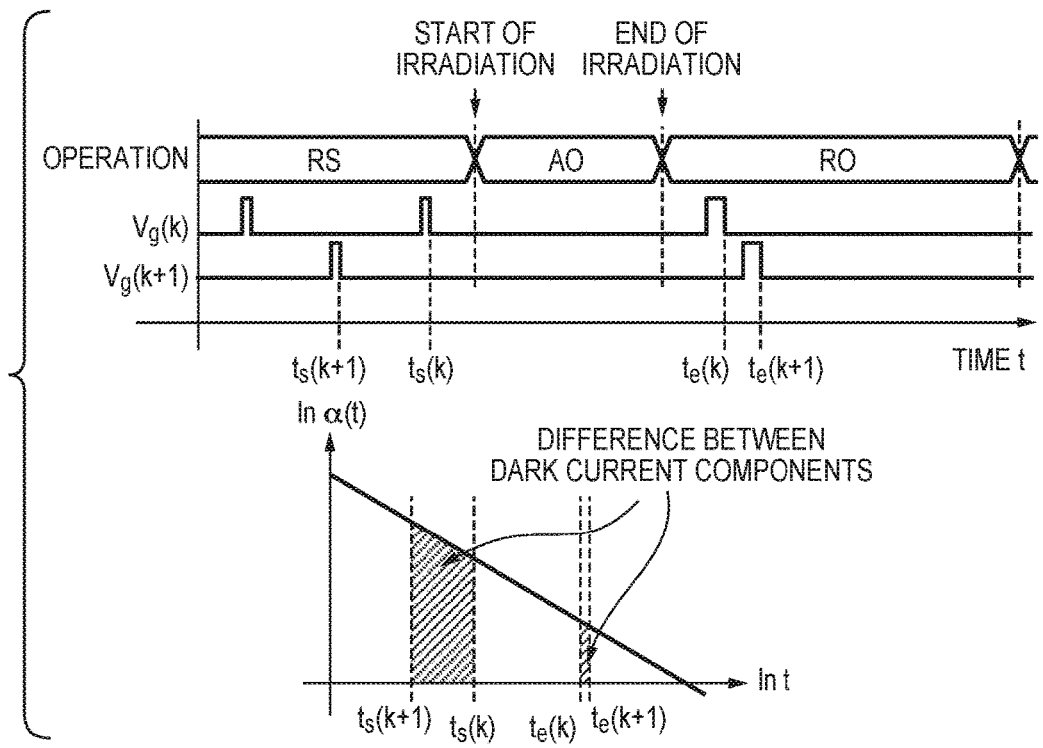

FIG. 6A shows a part of the driving timing chart (FIG. 4) of the first reference example, more specifically, a portion of the kth and (k+1)th rows. Similarly, FIG. 6B shows a part of the driving timing chart (FIG. 5) of the first example.

A period from the timing at which the last reset of the reset operation RS is performed to the timing at which the readout operation RO is performed will simply be referred to as "a period $T_A$" hereinafter. That is, in addition to the time of the accumulating operation AO, the period $T_A$ contains a time from the last reset of the reset operation RS to the start of the accumulating operation AO, and a time from the end of the accumulating operation AO to the start of the readout operation RO.

In the first reference example (FIG. 6A), the period $T_A$ for the kth row and that for the (k+1)th row are almost equal. In the first example (FIG. 6B), however, the period $T_A$ for the kth row and that for the (k+1)th row are different.

Noise such as the above-described dark current has dependence on time. For example, a noise component N1 contained in a signal from the sensor S can be represented by using time t as follows:

$$N1 = \int \alpha(t)dt \qquad (101)$$

where $\alpha(t)$ is a function depending on the time t, and given by a predetermined noise model.

For example, let ts(k) be the time at which the last reset of the reset operation RS is performed in the kth row, and te(k) be the time at which the readout operation RO is performed in the kth row. Also, let ts(k+1) be the time at which the last reset of the reset operation RS is performed in the (k+1)th row, and te(k+1) be the time at which the readout operation RO is performed in the (k+1)th row.

In this case, in the first reference example (FIG. 6A), the following expression holds:

$$\int_{ts(k)}^{te(k)} \alpha(t)dt \approx \int_{ts(k+1)}^{te(k+1)} \alpha(t)dt$$

On the other hand, in the first example (FIG. 6B), the following inequality holds:

$$\int_{ts(k)}^{te(k)} \alpha(t)dt < \int_{ts(k+1)}^{te(k+1)} \alpha(t)dt$$

Based on this, in the first example, correction for removing the noise component N1 can be performed on image data obtained from the imaging unit 10. Details of this correction will be described below.

In addition to the noise component N1, a signal from the sensor S can contain another noise component (a noise component N2) such as fixed pattern noise (FPN) caused by the sensor arrangement, element variations, or the like. In this case, a signal SS from the sensor S can be represented by:

$$SS = S0 + N1 + N2 \qquad (102)$$

where S0 is a signal component based on the amount of electric charge generated in the sensor S by radiation. Also, the signal SS can be represented by using equation (101) as follows:

$$SS = \int \alpha(t)dt + S0 + N2 \qquad (103)$$

A noise model resulting from the dark current is given by using, for example, a proportional constant a as follows:

$$\alpha(t) = a \times t^{-1} \quad (104)$$

Therefore, equation (103) can be represented by:

$$SS = \int (a \times t^{-1}) dt + S0 + N2 \quad (105)$$
$$= a \times \ln(te/ts) + S0 + N2$$

where ts: time at which the last reset of the reset operation RS is performed in a given row
te: time at which the readout operation RO is performed in a given row Each of the proportional constant a and noise component N2 can take a different value for each sensor S (each pixel). However, the present inventor has found that the proportional constants a of neighboring sensors are almost equal, and the noise components N2 of neighboring sensors are almost equal. On the other hand, the signal components S0 of neighboring sensors are almost equal in a region where the change in signal component is small (for example, a region of an image except for a portion which forms a contour).

For example, assuming that a signal from a sensor S(m, n) in the mth row and the nth column is a signal SS(m, n), and a signal from a sensor S(m+1, n) in the (m+1)th row and the nth column is a signal SS(m+1, n), they can be represented by:

$$SS(m, n) = S0(m, n) + N1(m, n) + N2(m, n) \quad (106)$$
$$= a(m, n) \times \ln\{te(m)/ts(m)\} + S0(m, n) + N2(m, n)$$
$$SS(m+1, n) = S0(m+1, n) + N1(m+1, n) + N2(m+1, n)$$
$$= a(m+1, n) \times \ln\{te(m+1)/ts(m+1)\} +$$
$$S0(m+1, n) + N2(m+1, n)$$
$$a(m, n) \approx a(m+1, n)$$
$$S0(m, n) \approx S0(m+1, n)$$
$$N2(m, n) \approx N2(m+1, n)$$

According to above-mentioned expression (106), the difference between the signals SS(m, n) and SS(m+1, n) can be represented by:

$$SS(m, n) - SS(m+1, n) = a(m, n) \times [\ln\{te(m)/ts(m)\} - \ln\{te(m+1)/ts(m+1)\}] \quad (107)$$

Therefore, the following equation holds:

$$a(m, n) = \{SS(m, n) - SS(m+1, n)\} / [\ln\{te(m)/ts(m)\} - \ln\{te(m+1)/ts(m+1)\}] \quad (108)$$

In the first example, the start times of the readout operations RO on neighboring rows are almost equal, but the times at which the last reset of the reset operation RS is performed on neighboring rows are different. Therefore, the following expressions hold:

$$te(m) \approx te(m+1)$$
$$ts(m) \neq ts(m+1) \quad (109)$$

Therefore, the following expression holds from expression (109):

$$a(m, n) \approx \{SS(m, n) - SS(m+1, n)\} / [\ln\{te(m)/ts(m)\} - \quad (110)$$
$$\ln\{te(m)/ts(m+1)\}]$$
$$= \{SS(m, n) - SS(m+1, n)\} / \ln\{ts(m+1)/ts(m)\}$$

Since a(m, n) is calculated as described above, a dark current α(t, m, n) in the sensor S(m, n) can be represented as follows by referring to expression (101) again:

$$\alpha(t, m, n) = a(m, n) \times t^{-1} \quad (111)$$

Accordingly, a noise component N1(m, n) of the signal SS(m, n) can be represented as follows from expression (111):

$$N1(m, n) = \int \alpha(t, m, n) dt \quad (112)$$
$$= a(m, n) \times \ln\{te(m)/ts(m)\}$$
$$= \{SS(m, n) - SS(m+1, n)\} \times \ln\{te(m)/ts(m)\} /$$
$$\ln\{ts(m+1)/ts(m)\}$$

From the foregoing, correction for removing the noise component N1(m, n) can be performed on the signal SS(m, n), and a corrected signal SS'(m, n) is obtained. The corrected signal SS'(m, n) is:

$$SS'(m, n) = SS(m, n) - N1(m, n) \quad (113)$$

In the first example as described above, the noise component N1 caused by the dark current can be calculated, and correction for removing the noise component N1 can be performed on the signal SS from the sensor S.

In the first example, the apparatus IA can further include, in order to perform the above-mentioned correction, a measurement unit for measuring the period $T_A$ (the time from the last reset of the reset operation RS to the start of the readout operation RO) of each row. The measurement result obtained by this measurement unit is supplied to the processing unit 50 together with image data obtained by the imaging unit 10. Note that the measurement unit can be formed in either the imaging unit 10 or control unit 40. Also, when the row driving order in the above-described reset operation RS or readout operation RO is predetermined, the period $T_A$ of each row can be specified. Therefore, no measurement unit need be used in this case.

Note that in the first reference example, both the reset operation RS and readout operation RO are performed by the progressive method. Accordingly, no difference is produced between the periods $T_A$ of neighboring rows (or the difference in period $T_A$ between neighboring rows is smaller than that in the first example). This makes it difficult to calculate the noise component N1 in the first reference example.

In the first example, the mode in which the reset operation RS is performed by the interlace method and the readout operation RO is performed by the progressive method is exemplified. However, the first example is not limited to this mode and can also be performed by another mode.

For example, as exemplarily shown in FIG. 7, it is also possible to perform the reset operation RS by the progressive method, and perform the readout operation RO by the interlace method. Since a difference is produced between the periods $T_A$ of neighboring rows in this method as well, it is possible to calculate the noise component N1, and correct a signal from the sensor S.

Also, as exemplarily shown in FIG. 8, it is possible to perform the reset operation RS by the interlace method for every two rows, and perform the readout operation RO by the progressive method. This method can achieve the same effects as described above, and can further shorten the initialization period of each sensor S in the reset operation RS. It is also possible to perform the interlaced reset operation RS for every three or more rows.

Furthermore, as exemplarily shown in FIG. 9, both the reset operation RS and readout operation RO can be performed by the interlace method. Although not shown, the interlaced reset operation RS and interlaced readout operation RO may also be performed such that the row driving orders are shifted by a half period. More specifically, reset is alternately performed on an even-numbered row and odd-numbered row in this order in the reset operation RS, and is alternately performed on an odd-numbered row and even-numbered row in this order in the readout operation RO. This method can increase the difference in period $T_A$ between neighboring rows.

That is, the reset operation RS and readout operation RO need only be so performed as to produce a difference in period $T_A$ between neighboring rows. In addition, as exemplified in the above-described interlace method, at least one of the reset operation RS and readout operation RO is preferably performed such that after a given row is driven, its neighboring row is driven after at least one other row is driven.

Note that in the first example, the mode in which a signal of the sensor S in a given row is corrected by using a signal of the sensor S in one of neighboring rows is exemplified. However, this correction may also be performed by using signals of the sensors S in both neighboring rows, or by using the average of these signals.

Note also that in the first example, the noise component caused by the dark current is described by exemplifying the simple noise model given by equation (101), in order to simplify the explanation. However, another noise model may also be used. In addition, the same explanation applies to another noise component having dependence on time.

Figure 10B:
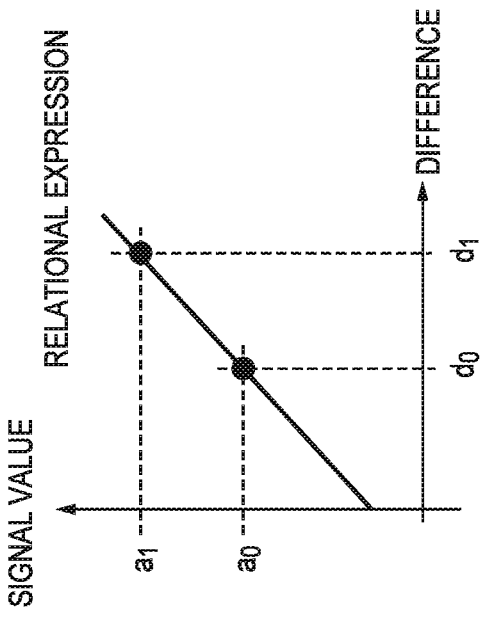
FIGS. 10A and 10B are views for explaining the relationship between a signal value difference and a noise component.
Figure 10A:
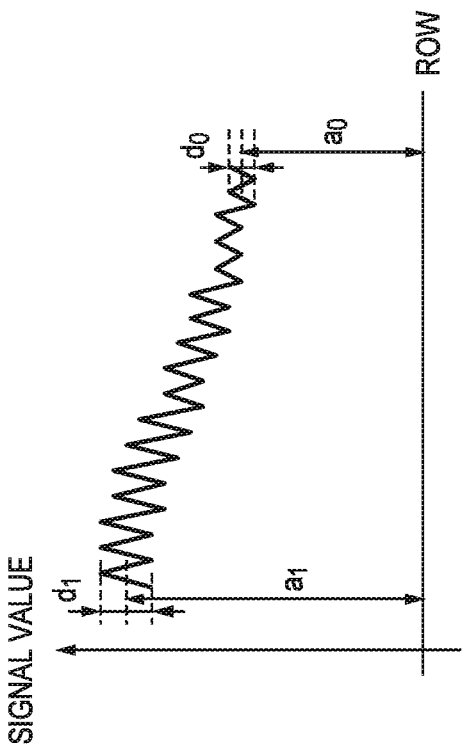

Furthermore, in the first example, the mode in which a correction coefficient (in the above-described example, the proportional constant a) is calculated as correction information by assuming a predetermined noise model is exemplified. However, it is also possible to calculate the correction coefficient without using any noise model. FIG. 10A shows the signal value (pixel value) of the sensor S in each row, in image data obtained beforehand separately from the readout operation RO. The abscissa indicates the number of a row in the sensor array 110, and the ordinate indicates the signal value. According to FIG. 10A, it is possible to obtain an average value a0 of the signal values of a given row and its neighboring row, a difference d0 between the signal values of the given row and its neighboring row, an average value a1 of the signal values of another row and its neighboring row, and a difference d1 between the signal values of the other row and its neighboring row. FIG. 10B is a plot graph based on the above-mentioned a0, a1, d0, and d1. The abscissa indicates the differences (d0 and d1) between the neighboring rows, and the ordinate indicates the average values (a0 and a1) of the signals in the individual rows. According to FIG. 10B, it is possible to predict a noise component having dependence on time and calculate its relational expression based on the average value and difference. The above-mentioned correction coefficient may also be calculated based on this relational expression. Note that this applies to each example to be described below.

(2-2. Second Example)

In the second example, correction for removing a noise component N2 is performed in addition to the above-described correction for removing the noise component N1. As described previously, the noise component N2 is caused by FPN or the like. This correction can be performed based on image data obtained by a readout operation O2 which is performed in a state in which no radiation is emitted, for example, before or after the readout operation RO. More specifically, imaging in a state in which no radiation is emitted is further performed before or after irradiation (before or after radiation imaging).

Figures 11A, 11B:
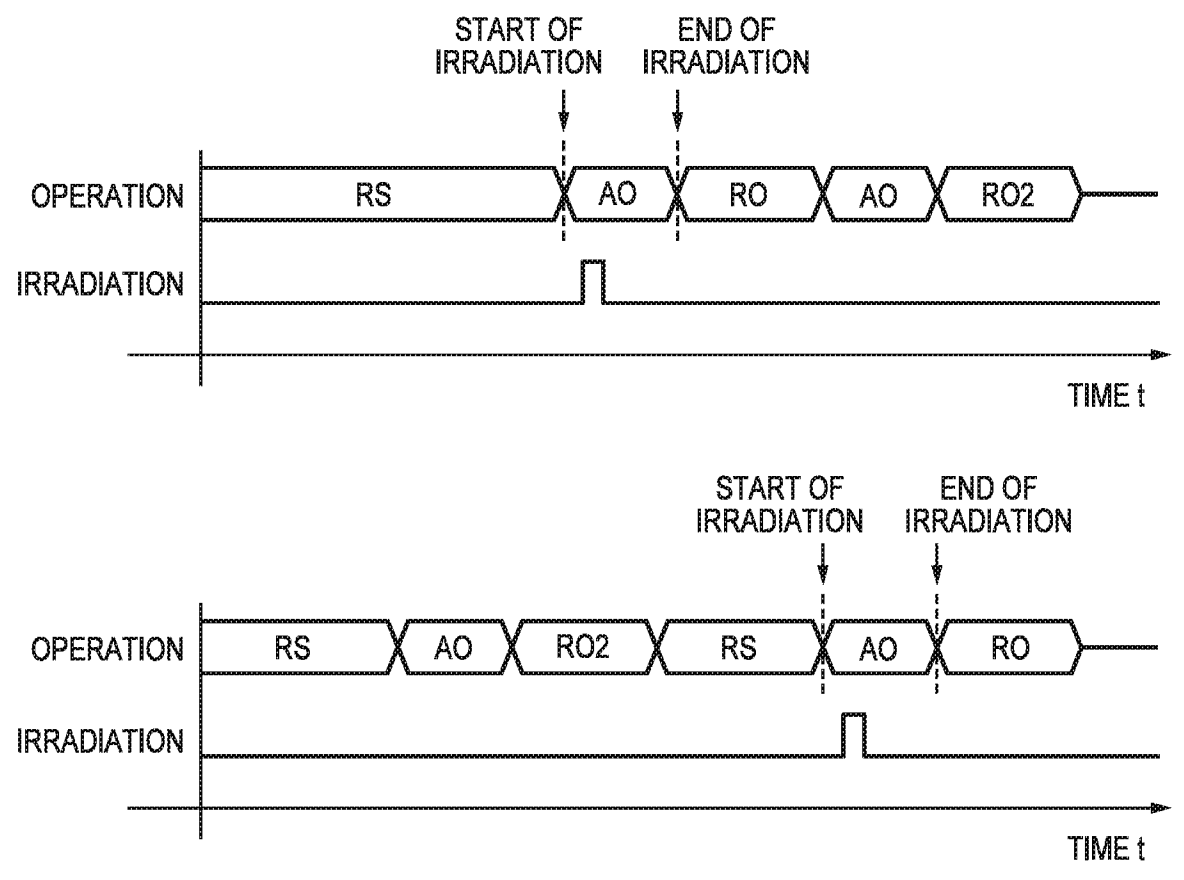

FIG. 11A shows a driving timing chart when the readout operation O2 is performed in a state in which no radiation is emitted, after the readout operation RO. FIG. 11B shows a driving timing chart when the readout operation O2 is performed in a state in which no radiation is emitted, before the readout operation RO. In the second example, image data obtained by the readout operation RO is corrected by using image data obtained by the readout operation RO2.

Let $SS_1(m, n)$ be a signal obtained from the sensor $S(m, n)$ in the mth row and the nth column by the readout operation RO, and $N1_1$ or the like be the noise component N1 or the like. In this case, the signal $SS_1(m, n)$ can be represented by:

$$SS_1(m, n) = SO_1(m, n) + N1_1(m, n) + N2_1(m, n) \quad (114)$$
$$= a(m, n) \times \ln\{t_1 e(m) / t_1 s(m)\} +$$
$$SO_1(m, n) + N2_1(m, n)$$

where $t_1 s(m)$ is time at which reset is performed in the mth row immediately before the readout operation RO, and $t_1 e(m)$ is time at which the readout operation RO is performed in the mth row.

Also, let $SS_2(m, n)$ be a signal obtained from the sensor $S(m, n)$ in the mth row and the nth column by the readout operation RO2, and $N1_2$ or the like be the noise component N1 or the like. In this case, the signal $SS_2(m, n)$ can be represented by:

$$SS_2(m, n) = N1_2(m, n) + N2_2(m, n) \quad (115)$$
$$= a(m, n) \times \ln\{t_2 e(m) / t_2 s(m)\} + N2_2(m, n)$$

where $t_2 s(m)$ is time at which reset is performed in the mth row immediately before the readout operation RO2, and $t_2 e(m)$ is time at which the readout operation RO2 is performed in the mth row.

A signal $SS_C(m, n)$ obtained by correcting the signal obtained by the readout operation RO based on the signal obtained by the readout operation RO2 can be represented by:

$$SS_C(m, n) \equiv SS_1(m, n) - SS_2(m, n) \quad (116)$$
$$= \{SO_1(m, n) + N1_1(m, n) + N2_1(m, n)\} -$$
$$\{N1_2(m, n) + N2_2(m, n)\}$$
$$= SO_1(m, n) + a(m, n) \times [\ln\{t_1 e(m) / t_1 s(m)\} -$$
$$\ln\{t_2 e(m) / t_2 s(m)\}]$$

In this case, the following expression holds:

$$N2_1(m, n) \approx N2_2(m, n) \tag{117}$$

After that, the above-described correction for removing the noise component N1 need only be performed on the corrected signal $SS_C(m, n)$ in the same manner as in the above-described first example.

That is, in the second example, correction for removing the noise component N2 is performed, and correction for removing the noise component N1 is performed on the image data obtained by the former correction by using the difference in period $T_A$ between neighboring rows. The second example can achieve the same effects as those of the above-described first example, and can further remove the noise component caused by FPN or the like.

(2-3. Third Example)

In the above-described first example, it is described that the signal components S0 of neighboring rows are almost equal in a region where the change in signal component is small (for example, a region of an image except for a portion which forms a contour). In this case, $S0(m, n) \approx S0(m+1, n)$ holds for the signal component $S0(m, n)$ of the sensor $S(m, n)$ in the mth row and the nth column and the signal component $S0(m+1, n)$ of the sensor $S(m+1, n)$ in the (m+1)th row and the nth column. In the first example, the calculating unit 52 of the processing unit 50 calculates, based on this expression, the correction coefficient for removing the noise component N1 from the difference in signal value between neighboring rows.

Since, however, the change in signal component is large in a contour formation portion of an image, $S0(m, n) \neq S0(m+1, n)$ holds. Accordingly, it is impossible to properly obtain the correction coefficient by the calculation method of the calculating unit 52. In this case, if the calculation result from the calculating unit 52 does not satisfy a predetermined condition, the correcting unit 51 does not adopt the calculation result as the correction coefficient, or can omit the correction process.

FIG. 12A is an enlarged plot graph of the signal value of the sensor S in the above-mentioned contour portion. In FIG. 12A, the abscissa indicates the number of a column in the sensor array 110, and the ordinate indicates the signal value. Referring to FIG. 12A, solid plots indicate signal values from the sensors S in the kth row, and hollow plots indicate signal values from the sensors S in the (k+1)th row. FIG. 12A demonstrates that the radiation doses sensed by the sensors S are larger and the signal values are larger in columns after the y1th column than in columns before the y1th column.

FIG. 12B is a plot graph showing the difference between the signal values of the sensors S in neighboring columns by rhomboid plots. According to FIG. 12B, the signal values are larger in columns after the y1th column than in columns before the y1th column, so the plot value is specifically large in the y1th column.

The processing unit 50 can further include a determination unit (not shown) for determining whether the above-mentioned difference plot value is smaller than a predetermined value. If the plot value is larger than the predetermined value, the plot value need not be used in the calculation of the correction coefficient, or the correction process can be omitted for that portion.

In this example, the mode in which whether the difference between the signals values of the sensors S in neighboring columns is smaller than the predetermined value is determined is exemplified. However, this determination may also be performed based on the statistics of the calculation results. For example, the above-mentioned determination unit may also determine whether a variation amount of the difference in signal value between neighboring columns is smaller than a predetermined value (for example, letting $\sigma$ be a standard deviation of variations from a median, whether the calculated difference is smaller than $\pm 3\sigma$ is determined).

In the third example described above, if the calculation result from the calculating unit 52 does not satisfy the predetermined condition, the correcting unit 51 of the processing unit 50 does not adopt the calculation result as the correction coefficient, or can omit the correction process. In the third example, therefore, correction for removing the noise component N1 can selectively be performed on an appropriate portion of image data. Note that the case in which the signal values largely change in the column direction of the sensor array 110 is exemplified in FIGS. 12A and 12B, but the same method applies to the row direction.

(2-4. Application Example)

In the above first to third examples, the mode in which the correction coefficient (in the first example, the proportional constant a) is calculated based on the difference in signal value between neighboring rows is exemplified. However, the present invention is not limited to this mode.

For example, assuming that a dark current $\alpha(m, n)$ is equal in one of the row direction and column direction of the sensor array 110, it is possible to correct shading of image data in the other of the row direction and column direction. For example, assuming that the dark current $\alpha(m, n)$ is equal in the row direction of the sensor array 110, a dark current in the xth row can be calculated from the difference in signal value between neighboring columns. Alternatively, assuming that the dark current $\alpha(m, n)$ is equal in the column direction of the sensor array 110, a dark current in the yth column can be calculated form the difference in signal values between neighboring rows.

It is also possible to divide the sensor array 110 into several groups G (not shown), and, assuming that a dark current $\alpha(G)$ in each group is equal, calculate the dark current $\alpha(G)$ in each group from the difference in signal value between neighboring groups. In this case, the sensor array 110 can be divided into the groups G for every two or more rows, for every two or more columns, or for every unit region including two or more rows and two or more columns. Furthermore, it is possible to assume that the dark current $\alpha$ is equal for all the sensors S in the sensor array 110. That is, the correction coefficient for correcting image data need only be obtained for every one or more groups, and the setting of the groups G can be changed in accordance with the imaging conditions, the imaging target, or the like.

In addition, one correction information can be determined by using signals from the sensors S in the groups G. For example, it is possible to use, as the correction coefficient, the mean of a plurality of calculation results obtained by using signals from the sensors S, or to use the median or mode as the correction coefficient instead of the mean. Furthermore, a standard deviation may also be used. That is, the correction coefficient can be calculated based on the statistics of a plurality of calculation results.

(3. Second Embodiment)

In the second embodiment, several examples of a moving image sensing mode and continuous imaging mode will mainly be exemplified below.

(3-1. Fourth Example)

Figure 13:
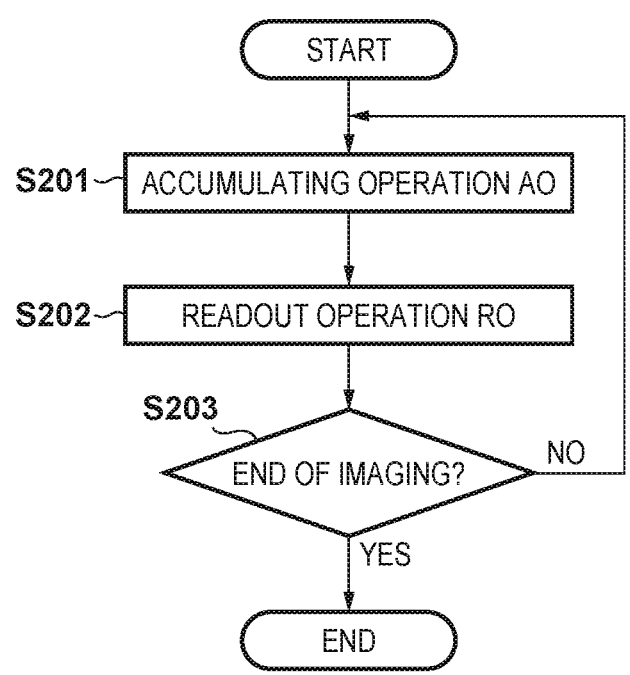
FIG. 13 is a flowchart for explaining an example of an operation of a radiation imaging apparatus.

FIG. 13 shows a flowchart for performing radiation imaging in, for example, the moving image sensing mode and continuous imaging mode. Radiation imaging like this is performed by emitting radiation a plurality of times. In this flowchart, steps S201 to S203 to be described below are mainly performed in accordance with the start of radiation imaging. In this specification, step S201 or the like will simply be referred to as "S201" hereinafter.

In S201, an accumulating operation AO of accumulating electric charge in each sensor S is started in accordance with given one-time irradiation. In the accumulating operation AO, a switching element W corresponding to each sensor S is kept OFF, so electric charge whose amount corresponds to the emitted radiation dose is accumulated. For example, the accumulating operation AO can be performed from the end of given one-time irradiation to the elapse of a predetermined period.

In S202, a readout operation RO of reading out a signal from each sensor S is performed in accordance with the end of the above-mentioned accumulating operation AO. The readout operation RO is performed by turning on corresponding switching elements W row by row. Consequently, a signal having a value corresponding to the amount of electric charge accumulated by the accumulating operation AO is read out from each sensor S.

In S203, whether to terminate imaging, more specifically, whether there is next irradiation is determined. If there is next irradiation, the process returns to S201. If there is no next irradiation, imaging is terminated. Note that the determination in this step can be performed based on, for example, imaging information preset by the user or the number of times of irradiation. It is also possible to terminate imaging if no next irradiation is started even when a predetermined time has elapsed after given irradiation is terminated.

In this flowchart, radiation for performing moving image sensing or continuous imaging is emitted a plurality of times, and a series of operations of the accumulating operation AO (S201) and the readout operation RO (S202) are performed in accordance with each irradiation. Signals corresponding to one-time irradiation are obtained from a plurality of sensors S by the above-mentioned series of operations. In this specification, the signals obtained from the sensors S by the series of operations are regarded as signals of one frame, and one image data is formed based on the signals of one frame.

Also, before a plurality of times of irradiation are started, a reset operation of initializing (resetting) each sensor S can repetitively be performed. Referring to FIG. 2 again, the driving method of the sensors S of the reset operation is the same as that of the readout operation RO in that a sensor driving unit 120 turns on the switching elements W row by row. In the reset operation, the switching element W is turned on while, for example, a column signal line 150 is connected to a reference potential by a switch (not shown). Alternatively, in the reset operation, the switching element W is turned on while, for example, (the feedback capacity of) a signal amplifier 130 is initialized. The electric charge thus generated in each sensor by noise such as a dark current before irradiation is released to the reference potential through the column signal line 150. It is also possible to sense the start of irradiation during the reset operation by monitoring the released electric charge or an electric current generated in accordance with the electric charge.

Figure 14:
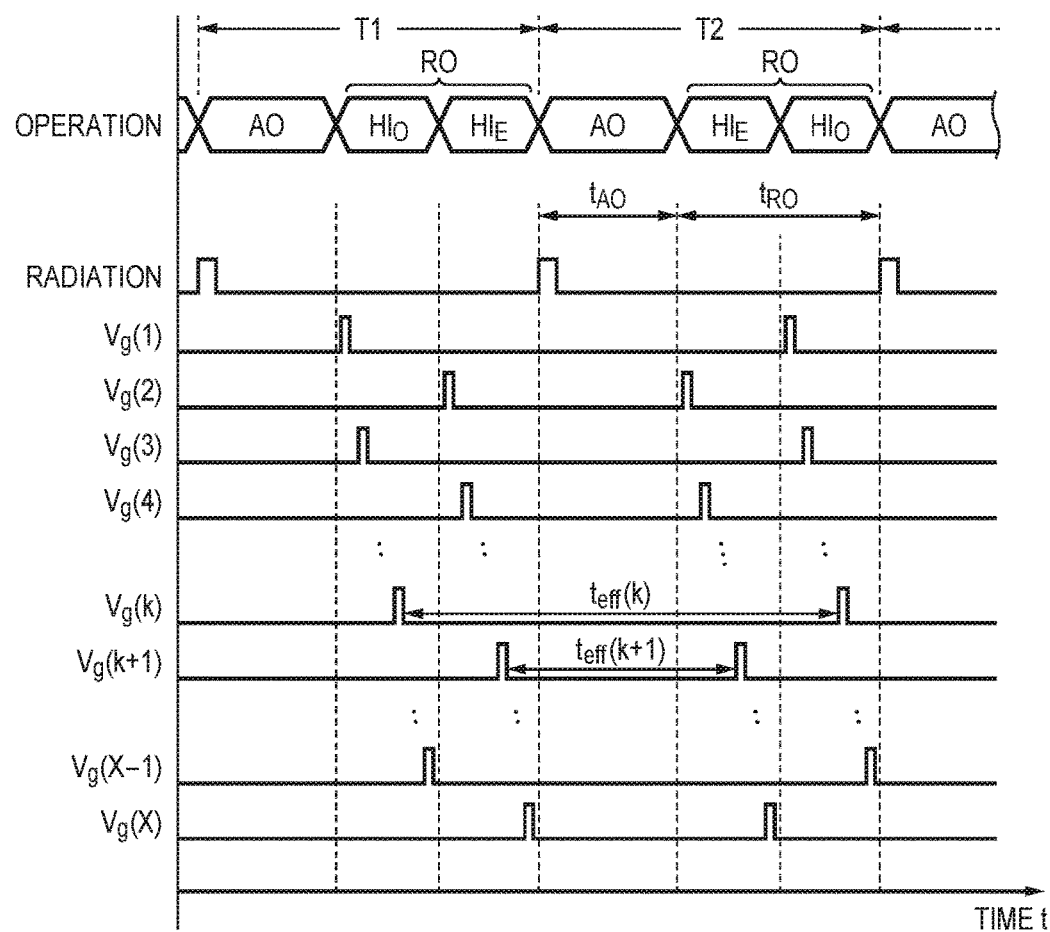
FIG. 14 is a timing chart for explaining an example of an operation of the radiation imaging apparatus.

FIG. 14 shows a driving timing chart of an imaging unit 10 including a sensor array 110 having X rows×Y columns in the fourth example. The abscissa is the time axis. The ordinate indicates signals Vg(1) to Vg(X) for driving the sensors S. For example, i is an integer from 1 to X, Vg(i) is a signal for driving the sensors S in the ith row. In this arrangement, Vg(i) is a signal for controlling ON/OFF of a corresponding switching element W. Each switching element W in the ith row is turned on when Vg(i) is at High level (H), and turned off when Vg(i) is at Low level (L).

FIG. 14 mainly shows a period T1 in which signals of a given one frame are obtained, and a period T2 in which signals of the next one frame are obtained. In each of the periods T1 and T2, the accumulating operation AO is performed when irradiation is performed once, and the readout operation RO is performed after that. In the fourth example, the readout operation RO is performed by the interlace method.

More specifically, the sensors S in one of an odd-numbered row and even-numbered row are driven first, and then the sensors S in the other of the odd-numbered row and even-numbered row are driven. Referring to FIG. 14, "$HI_O$" indicates an operation of driving the sensors S by sequentially selecting odd-numbered rows (the first row, the third row, the fifth row, . . . , the (X−1)th row). Also, "$HI_E$" indicates an operation of driving the sensors S by sequentially selecting even-numbered rows (the second row, the fourth row, the sixth row, . . . , the Xth row).

That is, the readout operation RO includes an operation $HI_O$ of reading out signals from the sensors S in an odd-numbered row, and an operation $HI_E$ of reading out signals from the sensors S in an even-numbered row. In the period T1 of FIG. 14, after the accumulating operation AO is performed, the readout operation RO is performed by performing the operation $HI_O$ first and then performing the operation $HI_E$. In the period T2, after the accumulating operation AO is performed, the readout operation RO is performed by performing the operation $HI_E$ first and then performing the operation $HI_O$.

Assume that a time from the readout operation RO in the period T1 to the readout operation RO in the period T2 in the sensors S in a given row is "a time $t_{eff}$". That is, the time $t_{eff}$ for a given row is a time from the timing at which the row is driven to read out signals of one frame in the period T1 to the timing at which the row is driven to read out signals of the next one frame in the period T2. Electric charge accumulated in the sensor S during the time $t_{eff}$ contains, for example, electric charge remaining before the period T1, and electric charge caused by noise such as a dark current, in addition to electric charge generated by the emitted radiation.

Let "$t_{eff}(k)$" be the time $t_{eff}$ of the kth row, "$t_{eff}(k+1)$" be the time $t_{eff}$ of the (k+1)th row, "$t_{AO}$" be the time required for the accumulating operation AO, and "$t_{RO}$" be the time required for the readout operation RO. In this case, the following equations hold:

$$t_{eff}(k)=3/2 \times t_{RO}+t_{AO},$$

$$t_{eff}(k+1)=1/2 \times t_{RO}+t_{AO} \qquad (201)$$

That is, in the driving method of the fourth example, a difference is produced between the times $t_{eff}$ of the kth and (k+1)th rows. Note that the case in which the kth row is an odd-numbered row is exemplified in this example, but the same can be said for a case in which the kth row is an even-numbered row.

In the fourth example, correction information for correcting a signal from the sensor S is calculated based on the above-described difference between the times $t_{eff}$.

Let S0 be a signal component based on the amount of electric charge generated in the sensor S by radiation. Also, let N1 be a noise component having dependence on time, for example, a noise component caused by electric charge remaining before the period T1, or a noise component caused by a dark current or the like. In addition, let N2 be a noise component having no dependence on time, for example, fixed pattern noise (FPN) caused by a sensor arrangement, element variations, or the like.

In this case, a signal SS from the sensor S can be represented by:

$$SS = S0 + N1 + N2 \tag{202}$$

The above-described noise component caused by electric charge remaining before the period T1 will be explained as an example of the cause of the noise component N1. This residual electric charge can be generated when electric charge is trapped in, for example, a lattice defect or dangling bond of the sensor S. The residual electric charge can disappear with the elapse of a sufficiently long time. In moving image sensing or continuous imaging exemplified in the fourth example, however, the signal readout operation RO is repetitively performed for a relatively short time, and this causes an afterimage in the image obtained in the period T2.

As one typical example given by a predetermined noise model, noise caused by this residual electric charge is given by:

$$\alpha(t) = a (\text{constant}) \tag{203}$$

In this case, the noise component N1 caused by the residual electric charge can be represented by using time t as follows:

$$N1 = \int \alpha(t) dt \tag{204}$$

Assuming that:
ts: time during which the readout operation RO is performed in the period T1, and
te: time during which the readout operation RO is performed in the period T2,
equation (204) can be represented by:

$$N1 = a \times (te - ts) \tag{205}$$

A constant a can take a different value for each sensor S (each pixel). However, the present inventors have found that the constants a of neighboring sensors are almost equal. Also, the noise components N2 of neighboring sensors are almost equal. In addition, the signal components S0 of neighboring sensors are almost equal in a region where the change in signal component is small (for example, a region of an image except for a portion which forms a contour).

For example, assume that a signal from a sensor S(m, n) in the mth row and the nth column is a signal SS(m, n), and a signal from a sensor S(m+1, n) in the (m+1)th row and the nth column is a signal SS(m+1, n). Assume also that the components S0, N1, and the like of each sensor S are S0(m, n), N1 (m, n), and the like. In this case, the following expressions hold from expressions (2) to (5):

$$\begin{aligned}
SS(m, n) &= S0(m, n) + N1(m, n) + N2(m, n) \\
&= a(m, n) \times \{te(m) - ts(m)\} + S0(m, n) + N2(m, n) \\
SS(m+1, n) &= S0(m+1, n) + N1(m+1, n) + N2(m+1, n) \\
&= a(m+1, n) \times \{te(m+1) - ts(m+1)\} + \\
&\quad S0(m+1, n) + N2(m+1, n) \\
a(m, n) &\approx a(m+1, n) \\
S0(m, n) &\approx S0(m+1, n) \\
N2(m, n) &\approx N2(m+1, n)
\end{aligned} \tag{206}$$

According to above-mentioned expression (206), the difference between the signals SS(m, n) and SS(m+1, n) can be represented by:

$$SS(m, n) - SS(m+1, n) = a(m, n) \times [\{te(m) - ts(m)\} - \{te(m+1) - ts(m+1)\}] \tag{207}$$

Therefore, the following equation holds:

$$a(m, n) = \{SS(m, n) - SS(m+1, n)\} / [\{te(m) - ts(m)\} - \{te(m+1) - ts(m+1)\}] \tag{208}$$

By using above-described expression (201), the following equations hold for k=m:

$$te(m) - ts(m) = t_{eff}(m) = 3/2 \times t_{RO} + t_{AO},$$

$$te(m+1) - ts(m+1) = t_{eff}(m+1) = 1/2 \times t_{RO} + t_{AO}$$

Accordingly, the following equation is calculated from above-mentioned expression (208):

$$a(m, n) = \{SS(m, n) - SS(m+1, n)\} / t_{RO} \tag{209}$$

Referring to expression (205) again, therefore, the noise component N1 caused by the electric charge remaining in the sensor S(m, n) can be calculated. More specifically, for the mth row (an odd-numbered row), the following equation holds:

$$N1(m, n) = \{SS(m, n) - SS(m+1, n)\} \times \{3/2 \times t_{RO} + t_{AO}\} / t_{RO} \tag{210a}$$

Also, for the (m+1)th row, the following equation holds:

$$N1(m+1, n) = \{SS(m, n) - SS(m+1, n)\} \times \{1/2 \times t_{RO} + t_{AO}\} / t_{RO} \tag{210b}$$

From the foregoing, correction for removing the noise component N1 (m, n) can be performed on the signal SS(m, n), and a corrected signal SS(m, n) is obtained. The corrected signal SS'(m, n) is:

$$SS'(m, n) = SS(m, n) - N1(m, n) \tag{211}$$

In the fourth example as described above, the noise component N1 caused by the electric charge remaining in the sensor S can be calculated, and correction for removing the noise component N1 can be performed on the signal SS from the sensor S. Note that in this example, the case in which the mth row is an odd-numbered row and the (m+1)th row is an even-numbered row is exemplified. Even in the opposite case, however, it is possible to calculate the constant a and noise component N1 following the same procedures.

Figure 15A:
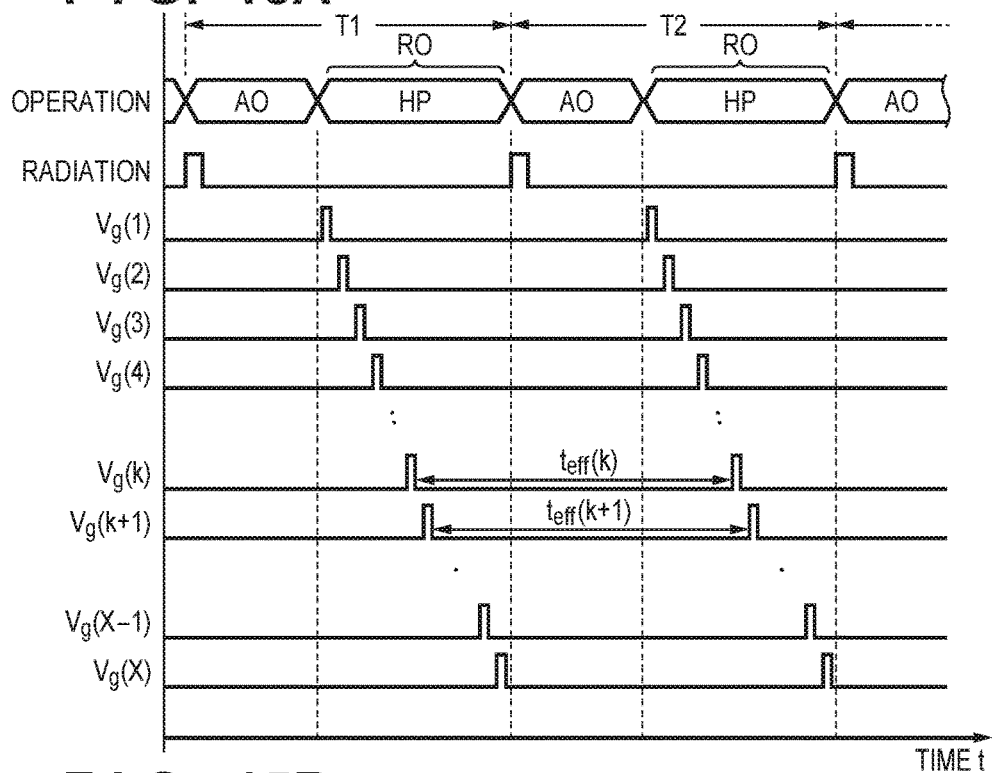
FIGS. 15A and 15B are timing charts for explaining examples of the operation of the radiation imaging apparatus.
Figure 15B:
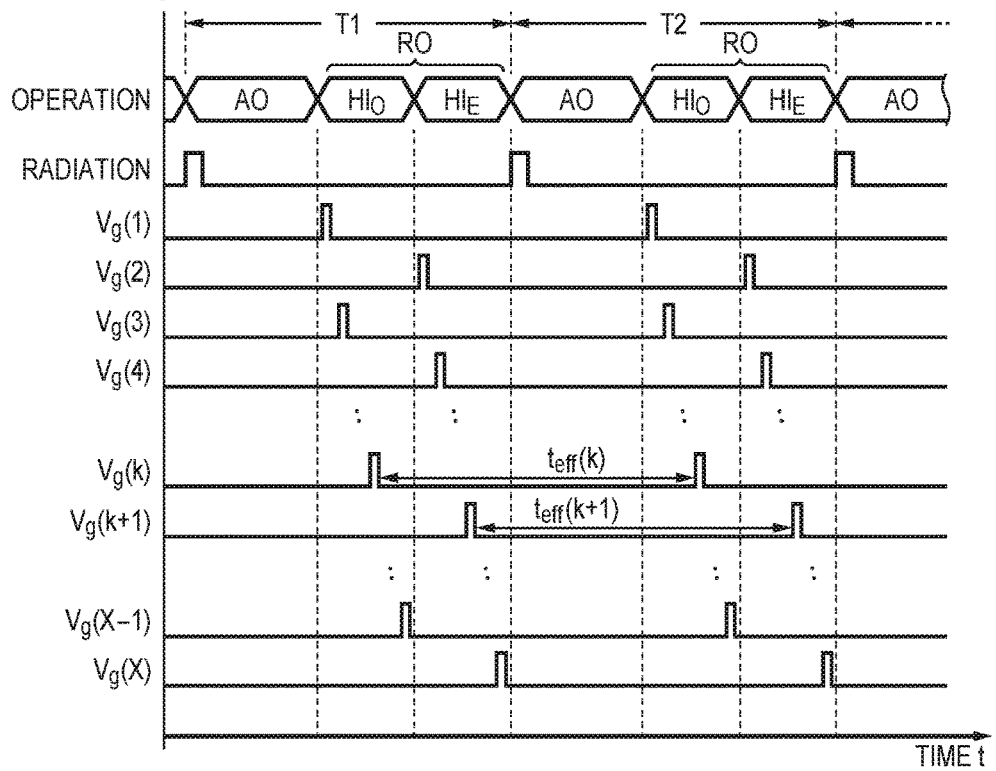

Reference examples of the driving method of the imaging unit 10 will be described be described below with reference to FIGS. 15A and 15B. FIGS. 15A and 15B show driving timing charts of the reference examples in the same manner as FIG. 14 described above.

FIG. 15A shows the second reference example. In the second reference example, the readout operation RO is performed by the progressive method after the accumulating operation AO is performed each time irradiation is performed. That is, in the second reference example, each readout operation RO is performed by driving the sensors S while sequentially selecting the first row, the second row, the third row, . . . , the Xth row. In FIG. 15A, "HP" indicates the operation of driving the sensors S by the progressive method. In the second reference example, the following equation holds:

$$t_{eff}(k) = t_{eff}(k+1) = t_{RO} + t_{AO}$$

In the second reference example, therefore, practically no difference is produced between the times $t_{eff}$ of the kth and (k+1)th rows.

FIG. 15B shows the third reference example. In the third reference example, the readout operation RO is performed by the interlace method after the accumulating operation AO is performed each time irradiation is performed. In the third reference example, each readout operation RO is performed by performing the operation $HI_O$ first and then performing the operation $HI_E$. Accordingly, the following equation holds:

$$t_{eff}(k)=t_{eff}(k+1)=t_{RO}+t_{AO}$$

In the third reference example, therefore, practically no difference is produced between the kth and (k+1)th rows.

In the second and third reference examples, practically no difference is produced between the times $t_{eff}$ of neighboring rows. This makes it difficult for the second and third reference examples to calculate the constant a (and the noise component N1).

On the other hand, in the fourth example, a given readout operation RO (the readout operation RO for obtaining signals of a given frame) and the next readout operation RO (the readout operation RO for obtaining signals of the next frame) are so performed as to produce a difference between the times $t_{eff}$ of neighboring rows. In the fourth example, the mode in which the repetitive readout operation RO is performed by alternately switching the operations $HI_O$ and $HI_E$ is exemplified. Then, the correction coefficient (in this example, the constant a of the noise component N1) is calculated as correction information based on the difference between the times $t_{eff}$. This makes it possible to calculate the noise component N1, and perform correction for removing the noise component N1 on the signal SS from the sensor S.

In the fourth example, the apparatus IA can further include, in order to perform the above-mentioned correction, a measurement unit for measuring the time $t_{eff}$ of each row. The measurement result obtained by this measurement unit is supplied to the processing unit 50 together with image data obtained by the imaging unit 10. The measurement unit can be formed in either the imaging unit 10 or control unit 40. Note that when the order of the operations $HI_O$ and $HI_E$ of the readout operation RO is determined, the time $t_{eff}$ of each row can be specified, so no measurement unit need be used in this case.

In the fourth example, the mode in which the correction information or the correction coefficient (in this example, the constant a) is calculated based on the difference in signal value between neighboring rows is exemplified. However, the present invention is not limited to this mode.

For example, it is also possible to divide the sensor array 110 into several regions R (not shown), and, assuming that the constant a(R) in each region R is equal, calculate the constant a(R) in each region R from the difference in signal value between two neighboring regions R. In this case, the sensor array 110 can be divided into the regions R for every two or more rows, for every two or more columns, or for every unit region including two or more rows and two or more columns. Furthermore, it is possible to assume that the constant a is equal for all the sensors S in the sensor array 110. That is, the correction information or correction coefficient need only be calculated for every one or more unit regions R, and the setting of the regions R can be changed in accordance with the imaging conditions, the imaging target, or the like.

Also, one correction information for a given region R may be determined by using signals from the sensors S in the region R. For example, it is possible to use, as the correction coefficient, the mean of a plurality of calculation results obtained by using signals from the sensors S in a given region R, or to use the median or mode as the correction coefficient instead of the mean. Furthermore, a standard deviation may also be used. That is, the correction coefficient can be calculated based on the statistics of a plurality of calculation results.

In addition, a target for which the correction information or the like is to be set is not limited to the above-mentioned region R in the sensor array 110. For example, it is possible to determine one correction information for every predetermined period of radiation imaging, for every predetermined times of the readout operation RO (for every predetermined number of frames), or the like, and correct two or more image data by using the same correction information.

Also, in the fourth example, the mode in which the correction information is calculated based on the difference between signals of the sensors S in neighboring rows is exemplified. However, this calculation need only be performed by using signals of the sensors S in neighboring rows, and may also be performed by using the mean of the signals.

Furthermore, in the fourth example, the noise component N1 is described by using the simple noise model of expression (202) in order to simplify the explanation. However, another noise model may also be used. In addition, the same method applies to another noise component having dependence on time, for example, a noise component caused by a dark current. For example, the noise model caused by the dark current can be given by $\beta(t)=b\times t^{-1}$ by using a constant b. That is, the constant (for example, the constant a) of the noise model need only be calculated based on the difference in time $t_{eff}$ between neighboring rows.

(3-2. Fifth Example)

In the above-described fourth example, the driving method which performs each readout operation RO by the interlace method so as to produce a difference in time $t_{eff}$ between neighboring rows. More specifically, one of the operations $HI_O$ and $HI_E$ is performed first and then the other is performed in a given readout operation RO, and the other one of the operations $HI_O$ and $HI_E$ is performed first and then one of them is performed in the next readout operation RO. However, the present invention is not limited to these driving methods.

Figure 16:
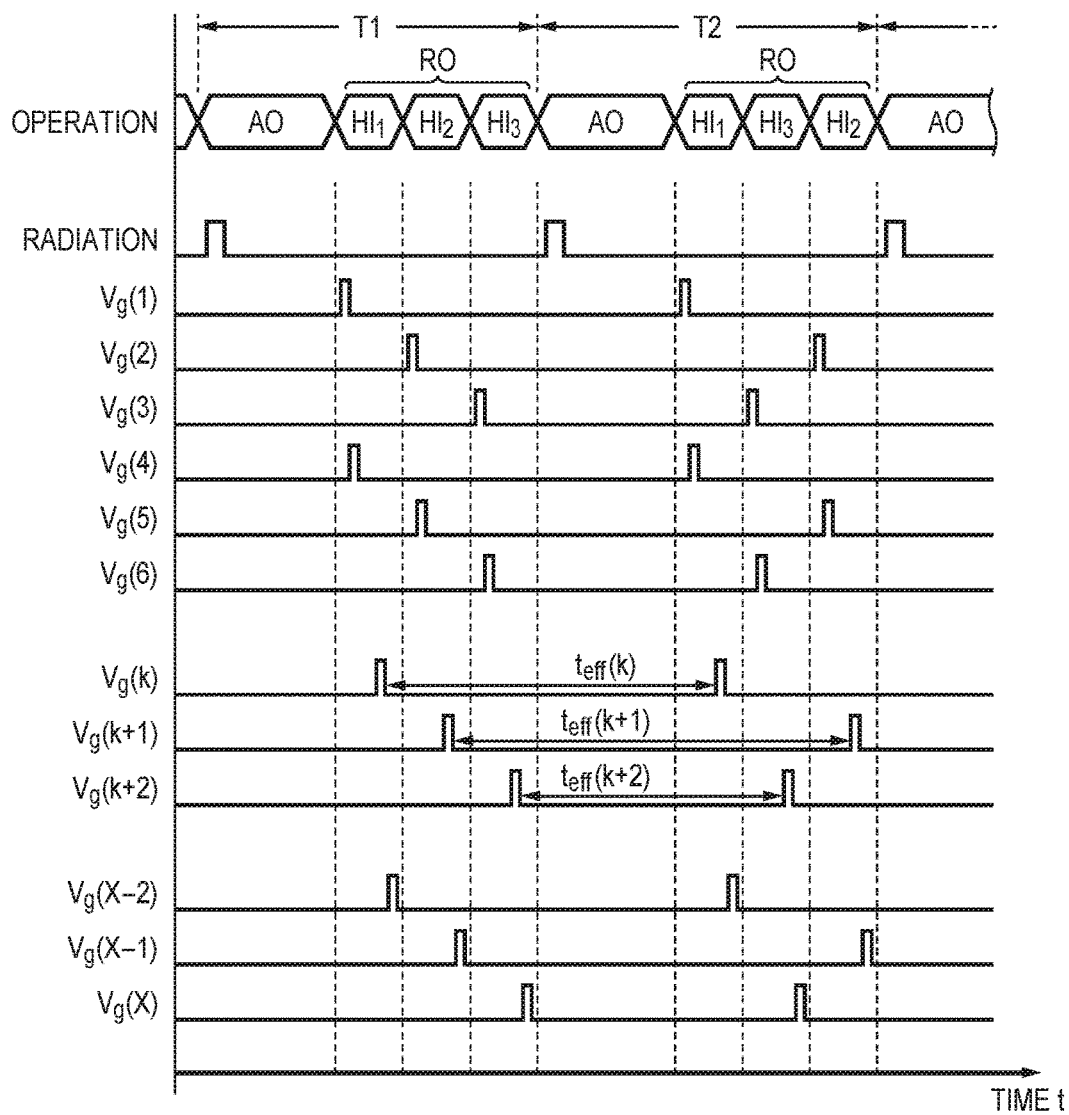
FIG. 16 is a timing chart for explaining an example of the operation of the radiation imaging apparatus.

FIG. 16 shows a driving timing chart of the fifth example in the same manner as the above-described fourth example (FIG. 14). In the fifth example, the readout operation RO is performed by an interlace method which selects rows three by three. More specifically, in the fifth example, the readout operation RO is performed by three types of operations $HI_1$ to $HI_3$. In the operation $HI_1$, the sensors S are driven by selecting rows in the order of the first row, the fourth row, the seventh row, . . . , the (X−2)th row. In the operation $HI_2$, the sensors S are driven by selecting rows in the order of the second row, the fifth row, the eighth row, . . . , the (X−1)th row. In the operation $HI_3$, the sensors S are driven by selecting rows in the order of the third row, the sixth row, the ninth row, . . . , the Xth row. According to FIG. 16, the readout operation RO in the period T1 is performed in the order of the operations $HI_1$, $HI_2$, and $HI_3$, and the readout operation RO in the period T2 is performed in the order of the operations $HI_1$, $HI_3$, and $HI_2$. Even the driving method like this produces a difference in time $t_{eff}$ between neighboring rows.

In another viewpoint, in the fifth example, the sensor array 110 (a plurality of arrayed sensors S) is divided into three groups row by row, and one row in a given group is neighboring to a row in another group. That is, the sensor array 110 is so divided that two neighboring rows belong to different groups. The readout operation RO is performed group by group. The control unit 40 can determine how to divide the sensor array 110 into groups. In this case, the control unit 40 functions as a divider. The control unit 40 may also include a determination unit (not shown) for determining how to divide the sensor array 110. The sensor array 110 need only be driven group by group by the driving unit 20 (more specifically, the sensor driving unit 102) based on, for example, a control signal from the control unit 40.

FIG. 16 shows a case in which k=3j−2 (k is an integer from 1 to X, and j is an integer of 1 or more) for the kth row, that is, a case in which the remainder is 1 when k is divided by 3. In this case, the following equations hold:

$$t_{eff}(k)=t_{RO}+t_{AO},$$

$$t_{eff}(k+1)=4/3 \times t_{RO}+t_{AO},$$

$$t_{eff}(k+2)=2/3 \times t_{RO}+t_{AO} \quad (212)$$

That is, a difference is produced in time $t_{eff}$ between neighboring rows.

As described above, each readout operation RO which produces a difference in time $t_{eff}$ between neighboring rows is not limited to the interlace method which alternately changes the order of the operations $HI_O$ and $HI_E$, and the same effect can be obtained by another interlace method. That is, it is only necessary to produce a difference in time $t_{eff}$ between neighboring rows by making the order of rows to be selected in a given readout operation RO different from the order of rows to be selected in the next readout operation RO.

As described above, it is possible to perform a given readout operation RO and the next readout operation RO so as to produce a difference in time $t_{eff}$ between neighboring rows in the fifth example as well. Then, the correction information or correction coefficient can be calculated based on the difference in time $t_{eff}$ following the same procedures as in the fourth example. Accordingly, the same effects as those of the fourth example can be obtained by the fifth example as well.

Note that the interlace method for every three rows is exemplified in this example in order to simplify the explanation, but an interlace method for every four or more rows may also be used. In addition, X need not be a multiple of 3. Furthermore, other parameters are also not limited to the exemplified quantities.

(3-3. Sixth Example)

In the above-described fourth and fifth examples, the driving methods which perform each readout operation RO by the interlace method so as to produce a difference in time $t_{eff}$ between neighboring rows are exemplified. However, the present invention is not limited to these driving methods.

Figure 17:
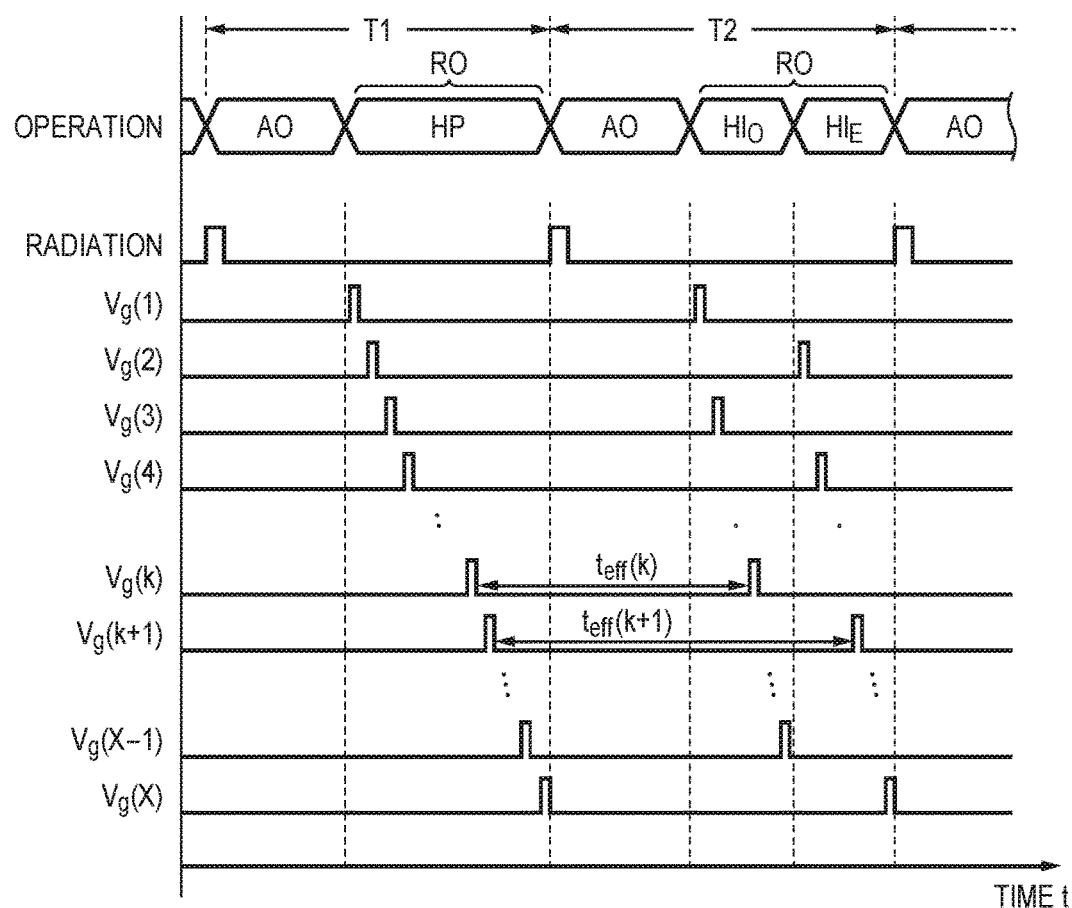
FIG. 17 is a timing chart for explaining an example of the operation of the radiation imaging apparatus.

FIG. 17 shows a driving timing chart of the sixth example in the same manner as the above-described fourth example (FIG. 14). The sixth example mainly differs from the fourth example in that the readout operation RO in the period T1 is performed by the progressive method (the operation HP), and the readout operation RO in the period T2 is performed by the interlace method (the operations $HI_O$ and $HI_E$). Also, the sixth example mainly differs from the above-described fifth example in that the readout operation RO is performed without dividing the sensor array 110 into groups in the period T1, and the readout operation RO is performed by performing this division in the period T2.

FIG. 17 exemplifies a case in which the kth row is an odd-numbered row. When the kth row is an odd-numbered row, the following equations hold:

$$t_{eff}(k)=\{1-(k-1)/2X\} \times t_{RO}+t_{AO},$$

$$t_{eff}(k+1)=\{3/2-k/2X\} \times t_{RO}+t_{AO} \quad (213)$$

This produces a difference in time $t_{eff}$ between neighboring rows. Note that the case in which the kth row is an odd-numbered row is exemplified in this example, but it is possible to calculate the constant a and noise component N1 following the same procedures when the kth row is an even-numbered row.

Thus, each readout operation RO which produces a difference in time $t_{eff}$ between neighboring rows is not limited to the interlace method, and the same effect can be obtained by alternately performing the interlace method and progressive method. That is, it is only necessary to produce a difference in time $t_{eff}$ between neighboring rows by making the order of rows to be selected in a given readout operation RO different from the order of rows to be selected in the next readout operation RO.

As described above, the correction information or correction coefficient can be calculated based on the difference in time $t_{eff}$ in the sixth example as well. Accordingly, the same effects as those of the fourth embodiment can be obtained by the sixth example as well.

(3-4. Seventh Example)

In the seventh example, correction for removing the noise component N2 is performed in addition to the above-described correction for removing the noise component N1. As described previously, the noise component N2 is a noise component having no dependence on time, for example, a noise component caused by FPN. This correction is performed based on image data obtained by a second readout operation RO2 which is performed in a state in which the apparatus IA is not irradiated, for example, before or after the start of irradiation. The second readout operation RO2 is performed by the same driving method as that for the above-described readout operation RO, but in a state in which the apparatus IA is not irradiated.

Let $SS_1(m, n)$ be a signal obtained from the sensor S(m, n) in the mth row and the nth column by the readout operation RO. In addition, let $S0_1(m, n)$, $N1_1(m, n)$, and the like be corresponding components S0, N1, and the like. In this case, the signal $SS_1(m, n)$ can be represented by:

$$SS_1(m, n) = S0_1(m, n) + N1_1(m, n) + N2_1(m, n) \quad (214)$$

$$= a(m, n) \times \{t_1 e(m) - t_1 s(m)\} +$$

$$S0_1(m, n) + N2_1(m, n)$$

Also, let $SS_2(m, n)$ be a signal obtained from the sensor S(m, n) in the mth row and the nth column by the readout operation RO2. In addition, let $S0_2(m, n)$, $N1_2(m, n)$, and the like be corresponding components S0, N1, and the like. In this case, the signal $SS_2(m, n)$ can be represented by:

$$SS_2(m, n) = N1_2(m, n) + N2_2(m, n) \quad (215)$$

$$= a(m, n) \times \{t_2 e(m) - t_2 s(m)\} + N2_2(m, n)$$

A signal $SS_C(m, n)$ obtained by correcting the signal obtained by the readout operation RO based on the signal obtained by the readout operation RO2 can be represented by:

$$SS_C(m, n) \equiv SS_1(m, n) - SS_2(m, n) \tag{216}$$
$$= \{S0_1(m, n) + N1_1(m, n) + N2_1(m, n)\} -$$
$$\{N1_2(m, n) + N2_2(m, n)\}$$
$$= S0_1(m, n) + a(m, n) \times [\{t_1e(m) - t_1s(m)\} -$$
$$\{t_2e(m) - t_2s(m)\}]$$

In this case, the following expression holds:

$$N2_1(m, n) \approx N2_2(m, n) \tag{217}$$

After that, the above-described correction for removing the noise component N1 need only be performed on the corrected signal $SS_C(m, n)$ in the same manner as in each of the above-described examples.

That is, in the seventh example, correction for removing the noise component N2 is performed, and correction for removing the noise component N1 is performed on the image data obtained by the former correction by using the difference in time $t_{eff}$ between neighboring rows. The seventh example can achieve the same effects as those of the above-described fourth example, and can further remove the noise component N2 caused by FPN or the like.

(4. Third Embodiment)

In the third embodiment, several examples of a case in which a technique which initializes each sensor S by irradiating a sensor array 110 of an imaging unit 10 with light is applied to the moving image sensing mode or continuous imaging mode exemplified in the above-described second embodiment will mainly be exemplified below.

(4-1. Eighth Example)

Figure 18:
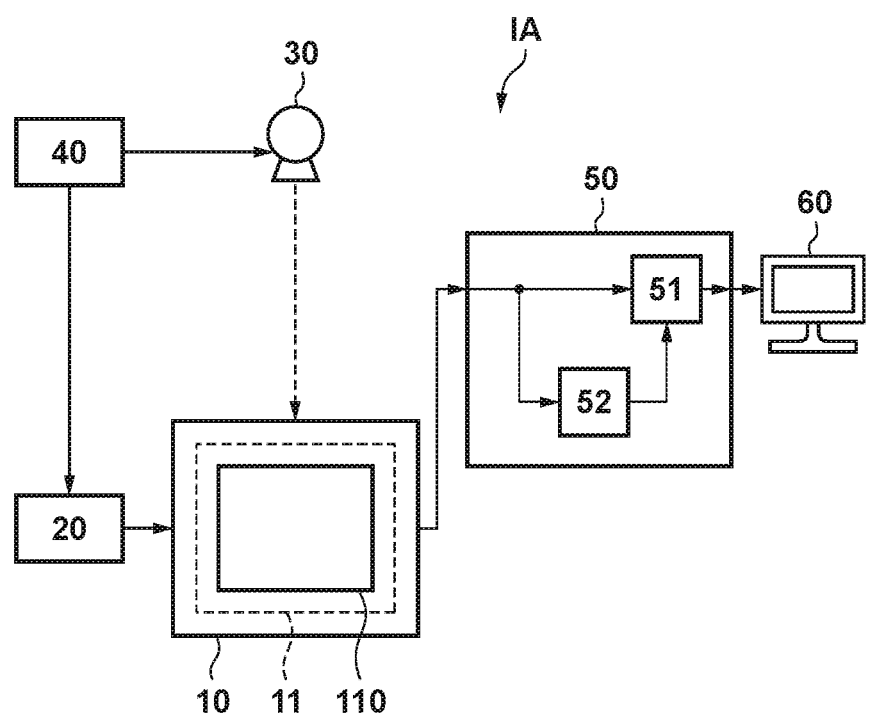
FIG. 18 is a view for explaining a system configuration example of a radiation imaging apparatus.

In the eighth example, as shown in FIG. 18, the imaging unit 10 further includes a light source 11 for irradiating the sensor array 110 with light. The light source 11 need only be able to irradiate each sensor of the sensor array 110 with a sufficient amount of light. The light source 11 is arranged on the back surface of the sensor array 110. For example, the light source 11 is so arranged as to overlap the sensor array 110 in a planar view (a planar view of the upper surface of the sensor array 110). Alternatively, the light source 11 may also be arranged outside the sensor array 110 along its outer periphery, or arranged near each corner of the sensor array 110, in a planar view. Furthermore, a member for propagating the light from the light source 11 to the whole area of the sensor array 110 may also be used together with the light source 11.

Figure 19:
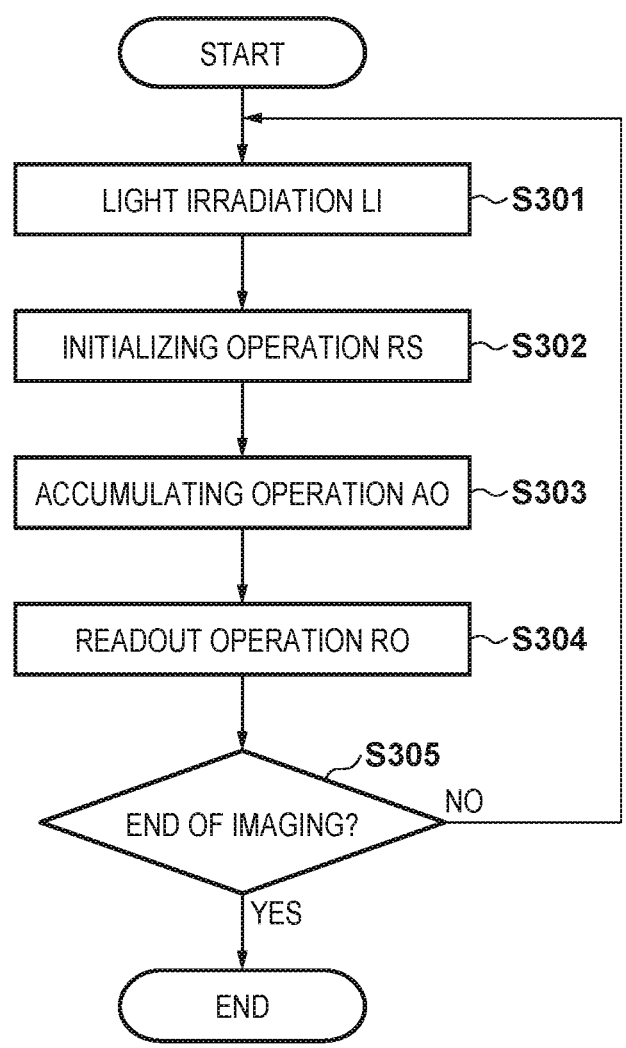
FIG. 19 is a flowchart for explaining an example of an operation of the radiation imaging apparatus.

FIG. 19 exemplarily shows a flowchart for performing radiation imaging. For example, radiation imaging in the moving image sensing mode, continuous imaging mode, or the like is performed by emitting radiation a plurality of times. In this flowchart, steps S301 to S305 to be described below are mainly performed. In this specification, step S301 or the like will simply be referred to as "S301" hereinafter. S301 to S304 are a series of steps for obtaining radiation data corresponding to one-time irradiation.

In S301, light irradiation LI for irradiating the sensor array 110 with light is performed. The light irradiation LI is performed by using the light source 11 described with reference to FIG. 18. In the light irradiation LI, a sufficient amount of light need only be emitted over a predetermined period such that electric charge is generated and accumulated in each sensor S by the emitted light, and the signal value of a sensor signal saturates.

In S302, an initializing operation RS of initializing (resetting) each sensor S of the sensor array 110 is performed in response to the completion of the light irradiation LI. In the initializing operation RS, each sensor S is initialized by removing the electric charge (or at least a portion of the electric charge) accumulated in the sensor S by the light irradiation LI.

In S303, in response to the completion of the initializing operation RS, a control signal (exposure enabling signal) which requests the start of irradiation is output to a radiation source or a radiation control unit for controlling the radiation source, thereby starting irradiation, and starting an accumulating operation AO of accumulating electric charge in each sensor S. In the accumulating operation AO, a switching element W corresponding to each sensor S is kept OFF, so electric charge whose amount corresponds to the emitted radiation dose is accumulated in the sensor S. For example, the accumulating operation AO is performed until a predetermined period elapses after the completion of one-time irradiation.

In S304, a readout operation RO of reading out a signal from each sensor S is performed in response to the completion of the above-mentioned accumulating operation AO. The readout operation RO is performed by turning on a corresponding switching element W row by row. Consequently, a signal having a value corresponding to the amount of electric charge accumulated by the accumulating operation AO is read out from each sensor S.

Referring to FIG. 2 again, the initializing operation RS in S302 and the above-mentioned readout operation RO are the same driving method in that a sensor driving unit 120 turns on the switching elements W row by row. In the initializing operation RS, the switching element W is turned on while, for example, a column signal line 150 is connected to a reference potential by a switch (not shown). Alternatively, in the initializing operation RS, the switching element W is turned on while, for example, (the feedback capacity of) a signal amplifier 130 is initialized. Consequently, the electric charge in each sensor S is released to the reference potential through the column signal line 150.

In S305, whether to terminate imaging, more specifically, whether there is next irradiation is determined. If there is next irradiation, the process returns to S301. If there is no next irradiation, imaging is terminated. Note that the determination in this step is performed based on, for example, imaging information preset by the user, or the number of times of irradiation. Imaging may also be terminated if no next irradiation is started even when a predetermined time has elapsed after given irradiation is complete. In this example, the mode in which irradiation is performed a plurality of times in the moving image sensing mode or continuous imaging mode is exemplified. In a still image sensing mode, for example, after radiation data corresponding to one-time irradiation is obtained, this imaging can be terminated without returning to S301.

In this flowchart, irradiation is performed a plurality of times when performing moving image sensing or continuous imaging, and irradiation is performed once when performing still image sensing. Then, the series operations, that is, the light irradiation LI (S301), initializing operation RS (S302), accumulating operation AO (S303), and readout operation RO (S304) corresponding to one-time irradiation are performed. By the series of operations, signals corresponding to one-time irradiation are obtained from a plurality of sensors S. In this specification, the signals obtained from the sensors S by the series of operations are regarded as signals of one frame (or a unit frame), and one image data is formed based on the signals of one frame.

When the initializing operation RS in S302 is performed after the light irradiation LI in S301 is performed so the signal values of sensor signals saturate, electric charges (residual electric charges) remaining in the sensors S are uniformly reduced. In moving image sensing or continuous imaging, for example, when the series of operations in S301 to S304 corresponding to signals of one given frame are started, electric charge generated when signals of an immediately preceding frame are read may remain in each sensor S. This residual electric charge may offset the characteristics of the sensor S, for example, may shift the threshold voltage of the switching element W as a TFT or shift the charge transfer efficiency of the switching element W. If the initializing operation RS is simply performed, therefore, a plurality of sensors S are not uniformly initialized in some cases. This residual electric charge may cause an afterimage in a radiation image based on signals of one frame read out after that.

In the eighth example, therefore, the light irradiation LI saturates a plurality of sensors S when performing the initializing operation RS. Then, the initializing operation RS uniformly reduces the residual electric charges in the sensors S. This makes it possible suppress an afterimage which may occur in the radiation image. Similarly, an afterimage can be suppressed in still image sensing as well by uniformly reducing the electric charges in the sensors S before the start of imaging by performing the light irradiation LI before the initializing operation RS.

The driving method (mainly the initializing operation RS in S302 and the readout operation RO in S304 described above) of the eighth example will be described below with reference to FIG. 20 and the like.

Figure 20:
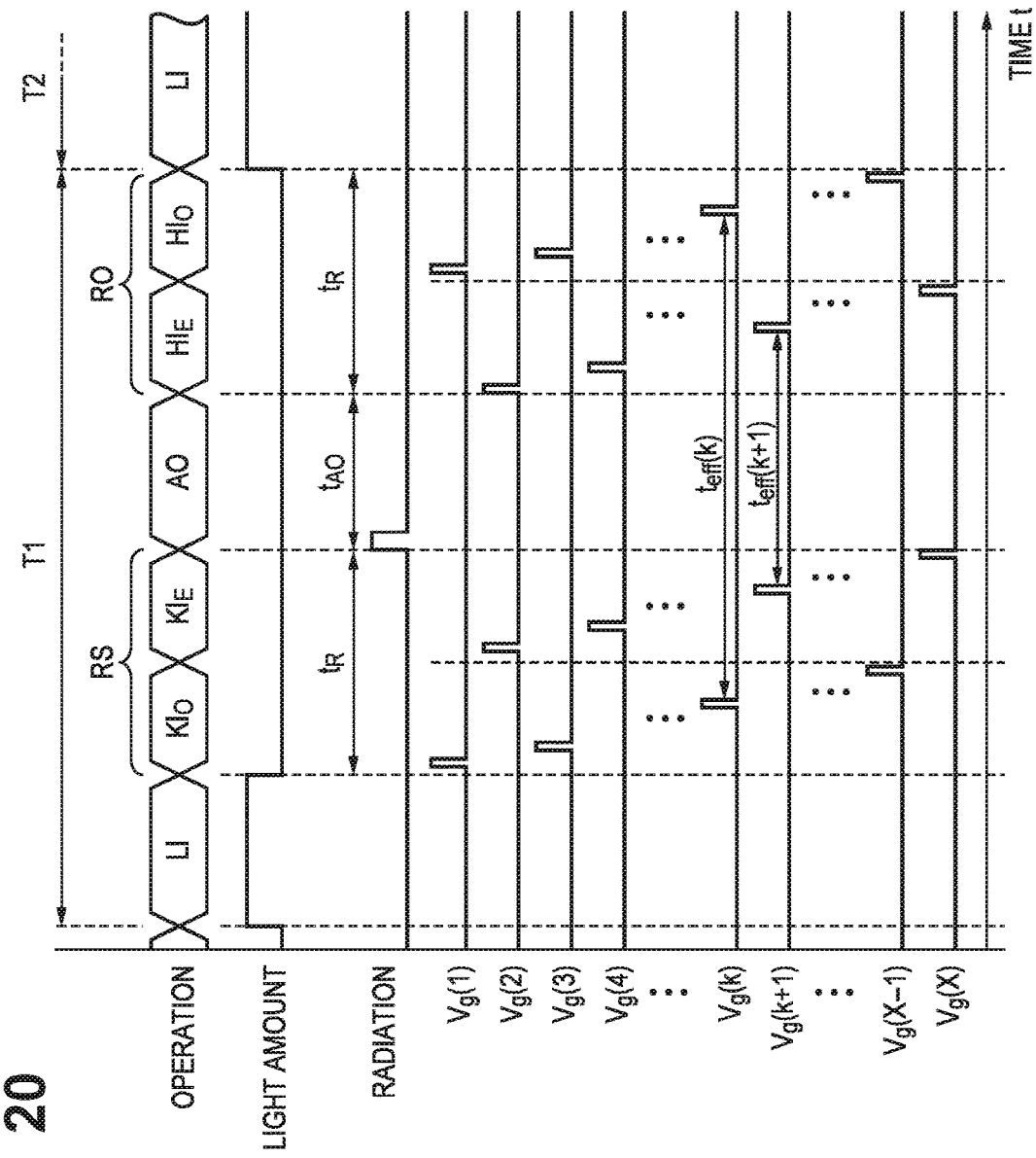
FIG. 20 is a timing chart for explaining an example of an operation of the radiation imaging apparatus.

FIG. 20 shows a driving timing chart of the imaging unit 10 including the sensor array 110 having X rows and Y columns. The abscissa indicates the time axis. The ordinate indicates signals Vg(1) to Vg(X) for driving the sensors S. For example, i is an integer from 1 to X, and Vg(i) is a signal for driving the sensors S in the ith row. In this arrangement, Vg(i) is a signal for controlling ON/OFF of a corresponding switching element W. Each switching element W in the ith row is turned on when Vg(i) is at High level (H), and turned off when Vg(i) is at Low level (L).

In this example, the period T1 for obtaining signals of one given frame will mainly be described. However, the same method applies to another period (for example, the period T2 for obtaining signals of the next one frame).

In the period T1, the series of operations in above-described S301 to S304 corresponding to one-time irradiation, more specifically, the light irradiation LI, initializing operation RS, accumulating operation AO, and readout operation RO are performed. In the eighth example, the initializing operation RS and readout operation RO are performed by the interlace method. More specifically, the sensors S in one of odd-numbered rows (the first row, the third row, the fifth row, . . . , the (X−1)th row) and even-numbered rows (the second row, the fourth row, the sixth row, . . . , the Xth row) are selected first, and then the sensors in the other of the odd-numbered rows and even-numbered rows are selected.

In the initializing operation RS shown in FIG. 20, "$KI_O$" indicates the operation of initializing the sensors S while sequentially selecting the odd-numbered rows, and "$KI_E$" indicates the operation of initializing the sensors S while sequentially selecting the even-numbered rows. Also, in the readout operation RO shown in FIG. 20, "$HI_O$" indicates the operation of initializing the sensors S while sequentially selecting the odd-numbered rows, and "$HI_E$" indicates the operation of initializing the sensors S while sequentially selecting the even-numbered rows.

That is, the initializing operation RS includes the operation $KI_O$ of initializing the sensors S in the odd-numbered rows, and the operation $KI_E$ of initializing the sensors S in the even-numbered rows. Also, the readout operation RO includes the operation $HI_O$ of reading out signals from the sensors S in the odd-numbered rows, and the operation $HI_E$ of reading out signals from the sensors S in the even-numbered rows.

In the period T1 shown in FIG. 20, the initializing operation RS is performed by performing the operation $KI_O$ first and then performing the operation $KI_E$. After that, the accumulating operation AO is performed, and the readout operation RO is performed by performing the operation $HI_E$ first and then performing the operation $HI_O$.

Assume that the time from the initializing operation RS to the readout operation RO in the period T1 in the sensor S in a given row is "a time $t_{eff}$". That is, the time $t_{eff}$ for one given row is the time from the initialization of the row to the driving of the row in the period T1.

Let "$t_{eff}(k)$" be the time $t_{eff}$ of the kth row, "$t_{eff}(k+1)$" be the time $t_{eff}$ of the (k+1)th row, "$t_R$" be the time required for the initializing operation RS, and "$t_{AO}$" be the time required for the accumulating operation AO. Also, to simplify the explanation, assume that the time required for the readout operation RO is equal to the time $t_R$ required for the initializing operation RS. In this case, the following equations hold:

$$t_{eff}(k) = 3/2 \times t_R + t_{AO},$$

$$t_{eff}(k+1) = 1/2 \times t_R + t_{AO} \tag{301}$$

That is, in the driving method of the eighth example, a difference is produced between the times $t_{eff}$ of the kth and (k+1)th rows. Note that the case in which the kth row is an odd-numbered row is exemplified in this example, but the same can be said for a case in which the kth row is an even-numbered row.

Note that in this example, the case in which the time required for the initializing operation RS and the time required for the readout operation RO are equal is exemplified in order to simplify the explanation. However, these times may also be different from each other. As an example, the pulse width of Vg(i) in the readout operation RO may also be made larger than that of Vg(i) in the initializing operation RS.

As described previously, the light irradiation LI and initializing operation RS can suppress an afterimage caused by the residual electric charges in the sensors S when signals of one immediately preceding frame are read out. However, when reading out signals of the next one frame, artifact may occur in a radiation image based on the signals. This artifact can be regarded as another afterimage caused when the light irradiation LI saturates a plurality of sensors S, and is a noise component having a relatively low frequency. In the eighth example, therefore, correction for reducing this noise component is performed by using correction information calculated based on the difference between the times $t_{eff}$ described above.

Note that it is in principle also possible to correct the afterimage caused by the residual electric charges in the sensors S when signals of one immediately preceding frame are read out, by using the correction information calculated based on the difference between the times $t_{eff}$. However, this afterimage contains information of an object (an afterimage of an object). Therefore, if the afterimage of the object contains a high-frequency noise component (for example, a steep edge in a contour portion), it may become difficult to perform correction by using the correction information calculated based on the difference between the times $t_{eff}$. The eighth example can suitably suppress even an afterimage containing this high-frequency noise component.

Let S0 be a signal component based on the amount of electric charge generated in the sensor S by radiation. Let N1 be a noise component having dependence on time, for example, a noise component caused by a dark current or the like. Let N2 be a noise component having no dependence on time, for example, fixed pattern noise (FPN) caused by the sensor arrangement, element variations, or the like.

In this case, the signal SS from the sensor S can be represented by:

$$SS=S0+N1+N2 \quad (302)$$

The noise component N1 can decrease when a sufficiently long time elapses. However, in moving image sensing or continuous imaging exemplified in the eighth example, the series of operations in S301 to S304 are repetitively performed within a relatively short time. Therefore, the noise component N1 causes an afterimage in an image corresponding to each frame.

The noise component N1 is given by a predetermined noise model. As one typical example, the noise component N1 is given by:

$$\alpha(t)=a \text{ (constant)} \quad (303)$$

In this case, the noise component N1 can be represented by using time t:

$$N1=\int\alpha(t)dt \quad (304)$$

Assuming that
ts: time during which the readout operation RO is performed in the period T1, and
te: time during which the readout operation RO is performed in the period T2,
the following equation holds:

$$N1=a\times(te-ts) \quad (305)$$

Although the constant a can take a different value for each sensor S (each pixel), the present inventors have found that the constants a of neighboring rows are almost equal. Also, the noise components N2 of neighboring rows are almost equal. Furthermore, the signal components S0 of neighboring sensors are almost equal in a region where the change in signal component is small (for example, a region of an image except for a portion which forms a contour).

For example, assume that a signal from a sensor S(m, n) in the mth row and the nth column is a signal SS(m, n), and a signal from a sensor S(m+1, n) in the (m+1)th row and the nth column is a signal SS(m+1, n). Also, let S0(m, n), N1(m, n), and the like be the components S0, N1, and the like corresponding to each sensor S. In this case, the following expressions hold from expressions (2) to (5):

$$SS(m, n) = S0(m, n) + N1(m, n) + N2(m, n) \quad (306)$$
$$= a(m, n) \times \{te(m) - ts(m)\} + S0(m, n) + N2(m, n)$$

$$SS(m+1, n) = S0(m+1, n) + N1(m+1, n) + N2(m+1, n)$$
$$= a(m+1, n) \times \{te(m+1) - ts(m+1)\} + S0(m+1, n) + N2(m+1, n)$$

-continued
$$a(m, n) \approx a(m+1, n)$$
$$S0(m, n) \approx S0(m+1, n)$$
$$N2(m, n) \approx N2(m+1, n)$$

According to above-mentioned expression (306), the difference between the signals SS(m, n) and SS(m+1, n) can be represented by:

$$SS(m, n)-SS(m+1, n)=a(m, n)\times[\{te(m)-ts(m)\}-\{te(m+1)-ts(m+1)\}] \quad (307)$$

Therefore, the following equation holds:

$$a(m, n)=\{SS(m, n)-SS(m+1, n)\}/[\{te(m)-ts(m)\}-\{te(m+1)-ts(m+1)\}] \quad (308)$$

When using above-described expression (301), the following equations hold for k=m:

$$te(m)-ts(m)=t_{eff}(m)=3/2\times t_R+t_{AO},$$

$$te(m+1)-ts(m+1)=t_{eff}(m+1)=1/2\times t_R+t_{AO}$$

Accordingly, the following equation is calculated from above-mentioned expression (308):

$$a(m, n)=\{SS(m, n)-SS(m+1, n)\}/t_R \quad (309)$$

Referring to expression (305) again, therefore, the noise component N1(m, n) of the sensor S(m, n) can be calculated. More specifically, for the mth row (an odd-numbered row), the following equation holds:

$$N1(m, n)=\{SS(m, n)-SS(m+1, n)\}\times\{3/2\times t_R+t_{AO}\}/t_R \quad (310a)$$

Also, in the (m+1)th row (an even-numbered row), the following equation holds:

$$N1(m+1, n)=\{SS(m, n)-SS(m+1, n)\}\times\{1/2\times t_R+t_{AO}\}/t_R \quad (310b)$$

From the foregoing, correction for removing the noise component N1 (m, From the foregoing, correction for reducing the noise component N1 (m, n) can be performed on the signal SS(m, n), and a corrected signal SS'(m, n) is obtained. The corrected signal SS'(m, n) is:

$$SS'(m, n)=SS(m, n)-N1(m, n) \quad (311)$$

In the eighth example described above, the noise component N1 can be calculated, and correction for reducing the noise component N1 can be performed on the signal SS from the sensor S. Note that in this example, the case in which the mth row is an odd-numbered row and the (m+1)th row is an even-numbered row is exemplified. However, it is possible to calculate the constant a and noise component N1 following the same procedures as above in the opposite case as well.

Figure 21A:
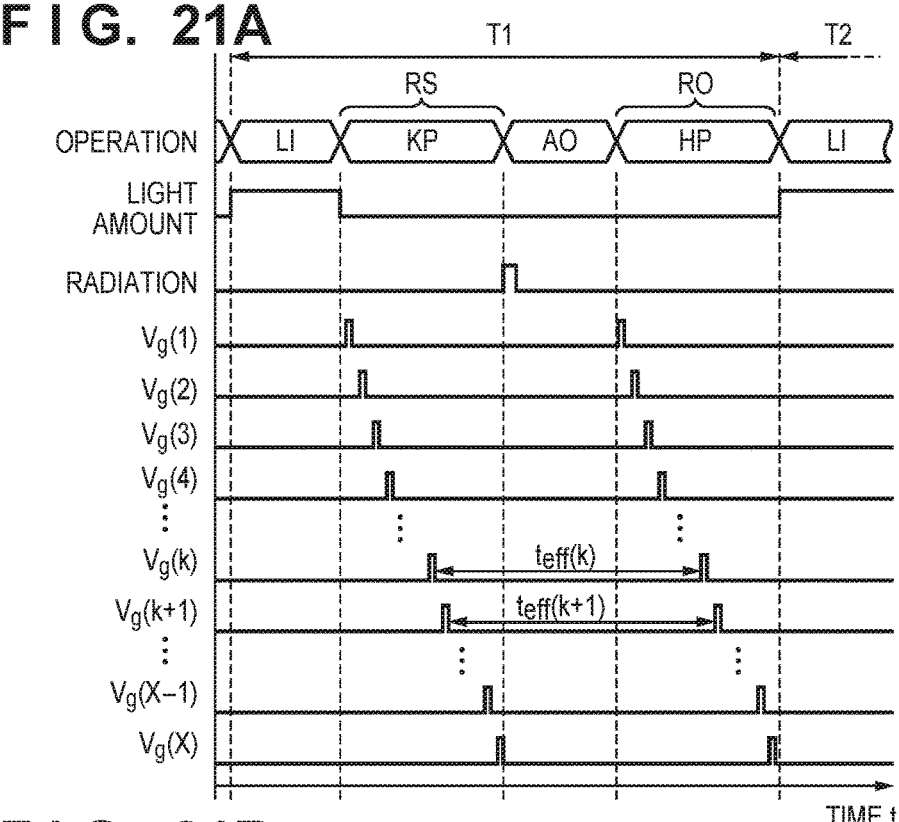
FIGS. 21A and 21B are timing charts for explaining examples of the operation of the radiation imaging apparatus.
Figure 21B:
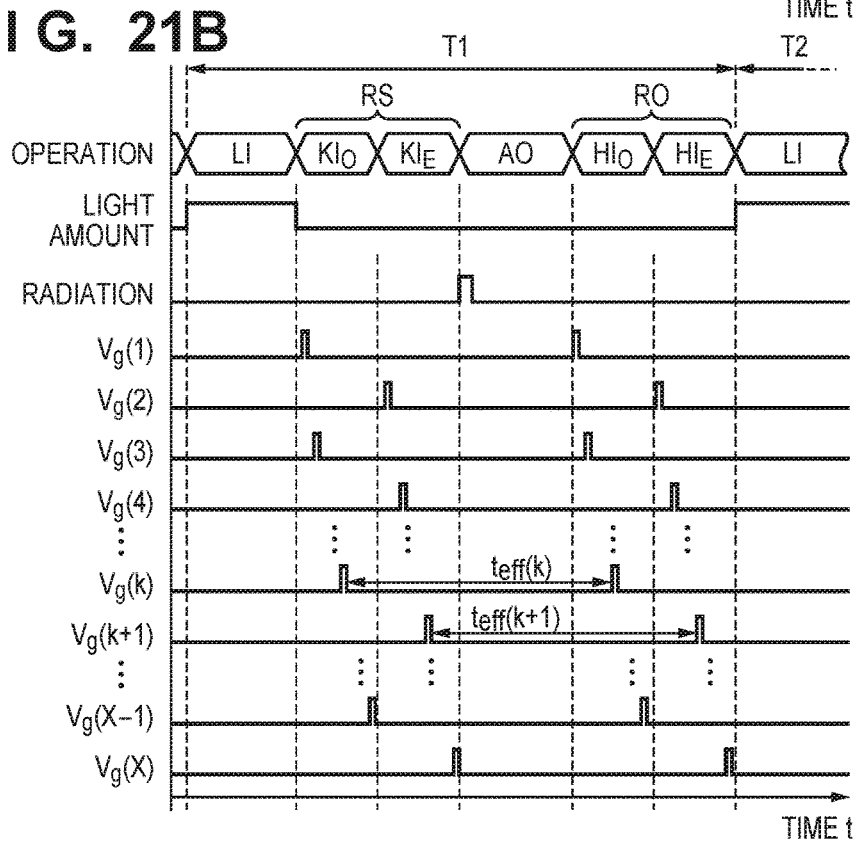

Reference examples of the driving method of the imaging unit 10 will be described below with reference to FIGS. 21A and 21B. FIGS. 21A and 21B show driving timing charts of the reference examples in the same manner as FIG. 20 described above.

FIG. 21A shows the fourth reference example. In the fourth reference example, the initializing operation RS and readout operation RO are performed by the progressive method. That is, the initializing operation RS is performed by initializing the sensors S while sequentially selecting the first row, the second row, the third row, . . . , the Xth row in the fourth reference example. Also, in the fourth reference example, the readout operation RO is performed by driving the sensors S while sequentially selecting the first row, the second row, the third row, . . . , the Xth row. Referring to FIG. 21A, "KP" indicates the operation of initializing the sensors S by the progressive method, and "HP" indicates the operation of driving the sensors S by the progressive method. In the fourth reference example, the following equation holds:

$$t_{\textit{eff}}(k)=t_{\textit{eff}}(k+1)=t_R+t_{AO}$$

In the fourth reference example, therefore, practically no difference is produced between the times $t_{\textit{eff}}$ of the kth and (k+1)th rows.

FIG. 21B shows the fifth reference example. In the fifth reference example, the initializing operation RS and readout operation RO are performed by the interlace method. More specifically, the initializing operation RS is performed by performing an operation $KI_O$ first and then performing an operation $KI_E$, and the readout operation RO is performed by performing an operation $HI_O$ first and then performing an operation $HI_E$. Accordingly, the following equation holds:

$$t_{\textit{eff}}(k)=t_{\textit{eff}}(k+1)=t_R+t_{AO}$$

In the fifth reference example, therefore, practically no difference is produced between the times $t_{\textit{eff}}$ of the kth and (k+1)th rows.

In the fourth and fifth reference examples, practically no difference is produced between the times $t_{\textit{eff}}$ of neighboring rows. Accordingly, it is difficult for the fourth and fifth reference examples to calculate the constant a (and the noise component N1).

On the other hand, in the eighth example, the series of operations for reading out signals of one given frame (that is, the series of operations from the initializing operation RS to the readout operation RO) are so performed as to produce a difference in time $t_{\textit{eff}}$ between neighboring rows. In the eighth example, the mode in which the initializing operation RS is performed by performing the operation $KI_O$ first and then performing the operation $KI_E$ and the readout operation RO is performed by performing the operation $HI_E$ first and then performing the operation $HI_O$ is exemplified. Then, the correction coefficient (in this example, the constant a of the noise component N1) is calculated as correction information based on the difference between the times $t_{\textit{eff}}$. This makes it possible to calculate the noise component N1, and perform correction of reducing the noise component N1 on the signal SS from the sensor S.

In the eighth example, the apparatus IA can further include a measurement unit for measuring the time $t_{\textit{eff}}$ of each row in order to perform the above-described correction. The measurement result obtained by this measurement unit is supplied to the processing unit 50 together with image data obtained by the imaging unit 10. The measurement unit can be formed in either the imaging unit 10 or control unit 40. Note that when the order of the operations $HI_O$ and $HI_E$ of the readout operation RO is determined, it is possible to specify the time $t_{\textit{eff}}$ of each row, so no measurement unit needs to be used in this case.

In the eighth example described above, the initializing operation RS is performed after the signal value of the signal of each sensor S is saturated by the light irradiation LI, thereby initializing a plurality of sensors S and uniformizing the states of the plurality of initialized sensors S. Consequently, it is possible to suppress an afterimage caused by the residual electric charge in each sensor S from being generated in a radiation image based on a frame obtained after that. Then, the readout operation RO is so performed as to produce a difference between the times $t_{\textit{eff}}$ of neighboring rows. In the eighth example, the mode in which the initializing operation RS by performing the operation $KI_O$ first and then performing the operation $KI_E$ and the readout operation is performed by performing the operation $HI_E$ first and then performing the operation $HI_O$ is exemplified. Correction for reducing the noise component N1 having dependence on time is performed on the sensor signal obtained by the readout operation RO based on the above-mentioned difference in time $t_{\textit{eff}}$ between neighboring rows. Accordingly, it is possible to prevent artifact caused by the light irradiation LI from being generated in the radiation image, and improve the quality of the radiation image.

Note that in the eighth example, the mode in which the correction information or correction coefficient (in this example, the constant a) is calculated based on the difference in signal value between neighboring rows is exemplified. However, the present invention is not limited to this mode.

For example, it is also possible to divide the sensor array 110 into several regions R (not shown), and, assuming that the constant a(R) in each region R is equal, calculate the constant a(R) in each region R from the difference in signal value between two neighboring regions R. In this case, the sensor array 110 can be divided into the regions R for every two or more rows, for every two or more columns, or for every unit region including two or more rows and two or more columns. Furthermore, it is possible to assume that the constant a is equal for all the sensors S in the sensor array 110. That is, the correction information or correction coefficient need only be calculated for every one or more unit regions R, and the setting of the regions R can be changed in accordance with the imaging conditions, the imaging target, or the like.

Also, one correction information for a given region R may be determined by using signals from the sensors S in the region R. For example, it is possible to use, as the correction coefficient, the mean of a plurality of calculation results obtained by using signals from the sensors S in a given region R, or to use the median or mode as the correction coefficient instead of the mean. Furthermore, a standard deviation may also be used. That is, the correction coefficient can be calculated based on the statistics of a plurality of calculation results.

In addition, a target for which the correction information or the like is to be set is not limited to the above-mentioned region R in the sensor array 110. For example, it is possible to determine one correction information for every predetermined period of radiation imaging, for every predetermined times of the readout operation RO (for every predetermined number of frames), or the like, and correct two or more image data by using the same correction information.

Also, in the eighth example, the mode in which the correction information is calculated based on the difference between signals of the sensors S in neighboring rows is exemplified. However, this calculation need only be performed by using signals of the sensors S in neighboring rows, and may also be performed by using the mean of the signals.

Furthermore, in the eighth example, the noise component N1 is described by using the simple noise model of expression (302) in order to simplify the explanation. However, another noise model may also be used. For example, a noise model caused by a dark current can be given by $\beta(t)=b \times t^{-1}$ by using a constant b. That is, the constant (for example, the constant a) of the noise model need only be calculated based on the difference in time $t_{\textit{eff}}$ between neighboring rows.

(4-2. Ninth Example)

In the above-mentioned eighth example, the mode in which the initializing operation RS is performed by performing the operations $KI_O$ and $KI_E$ in this order and the readout operation RO is performed by performing the operations $HI_E$ and $HI_O$ in this order so as to produce a difference in time $t_{\mathit{eff}}$ between neighboring rows is exemplified. However, the present invention is not limited to this mode, and the initializing operation RS and readout operation RO may also be performed by selecting rows in other orders.

Figure 22:
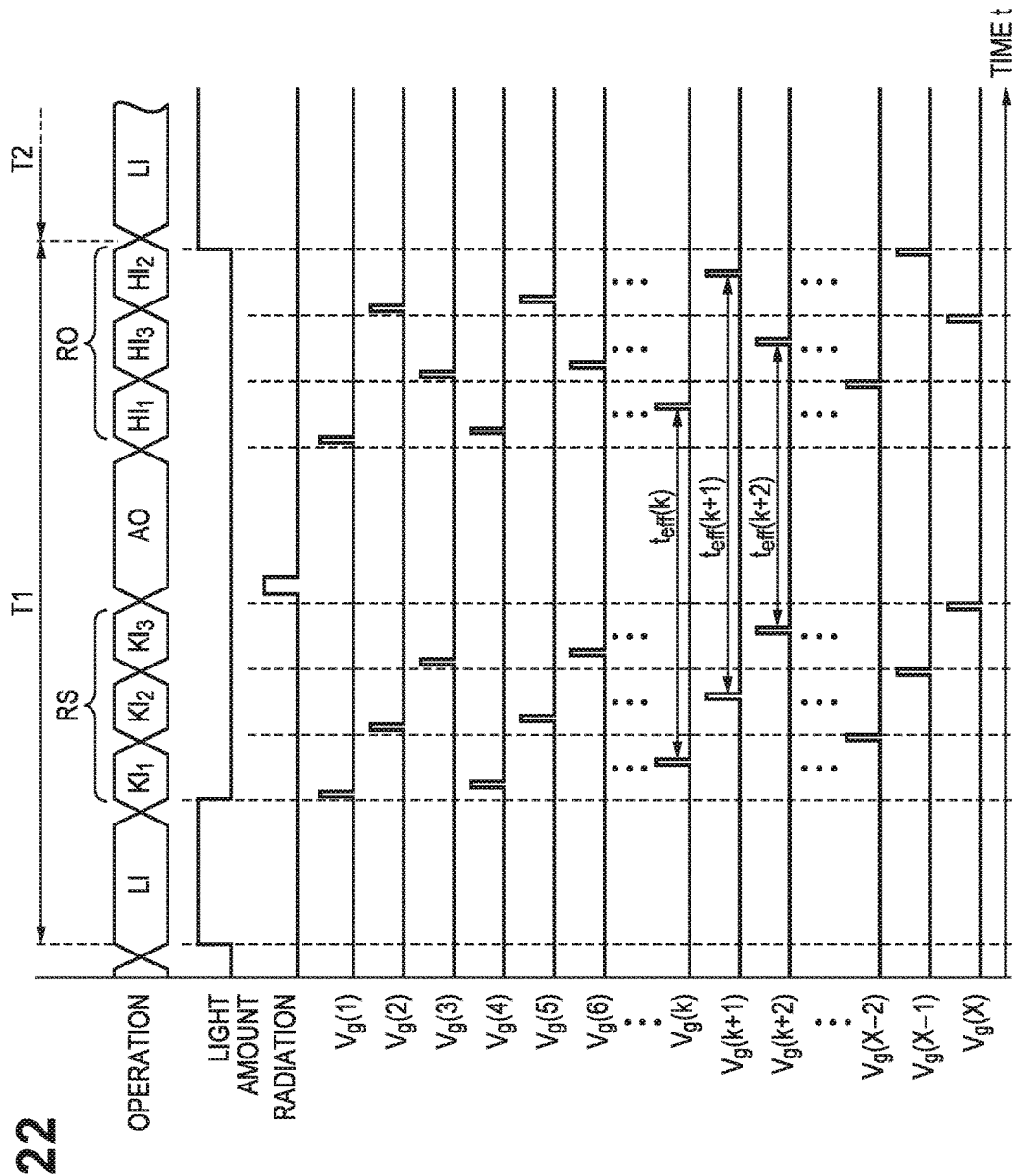
FIG. 22 is a timing chart for explaining an example of the operation of the radiation imaging apparatus.

FIG. 22 shows a driving timing chart of the ninth example in the same manner as the above-described eighth example (FIG. 20). In the ninth example, each of the initializing operation RS and readout operation RO is performed by an interface method which selects rows three by three. More specifically, in the ninth example, the initializing operation RS is performed by three types of operations $KI_1$ to $KI_3$, and the readout operation RO is performed by three types of operations $HI_1$ to $HI_3$.

In the operation $KI_1$, the sensors S are initialized while selecting rows in the order of the first row, the fourth row, the seventh row, . . . , the (X−2) row. In the operation $KI_2$, the sensors S are initialized while selecting rows in the order of the second row, the fifth row, the eighth row, . . . , the (X−1) row. In the operation $KI_3$, the sensors S are initialized while selecting rows in the order of the third row, the sixth row, the ninth row, . . . , the X row. In the operation $HI_1$, the sensors S are driven by selecting rows in the order of the first row, the fourth row, the seventh row, . . . , the (X−2)th row. In the operation $HI_2$, the sensors S are driven by selecting rows in the order of the second row, the fifth row, the eighth row, . . . , the (X−1)th row. In the operation $HI_3$, the sensors S are driven by selecting rows in the order of the third row, the sixth row, the ninth row, . . . , the Xth row.

According to FIG. 22, the initializing operation is performed in the order of the operations $KI_1$, $KI_2$, and $KI_3$, and the readout operation RO is performed in the order of the operations $HI_1$, $HI_3$, and $HI_2$. Even the driving method like this produces a difference in time $t_{\mathit{eff}}$ between neighboring rows.

In another viewpoint, in the ninth example, the sensor array 110 (a plurality of arrayed sensors S) is divided into three groups row by row, and one row in a given group is neighboring to a row in another group. That is, the sensor array 110 is so divided that two neighboring rows belong to different groups. The initializing operation RS and readout operation RO are performed group by group. The control unit 40 can determine how to divide the sensor array 110 into groups. In this case, the control unit 40 functions as a divider. The control unit 40 may also include a determination unit (not shown) for determining how to divide the sensor array 110. The sensor array 110 need only be driven group by group by the driving unit 20 (more specifically, the sensor driving unit 102) based on, for example, a control signal from the control unit 40.

FIG. 22 shows a case in which k=3j−2 (k is an integer from 1 to X, and j is an integer of 1 or more) for the kth row, that is, a case in which the remainder is 1 when k is divided by 3. In this case, the following equations hold:

$$t_{\mathit{eff}}(k) = t_R + t_{AO}$$

$$t_{\mathit{eff}}(k+1) = 4/3 \times t_R + t_{AO}$$

$$t_{\mathit{eff}}(k+2) = 2/3 \times t_R + t_{AO} \quad (312)$$

That is, a difference is produced in time $t_{\mathit{eff}}$ between neighboring rows.

As described above, the driving method which produces a difference in time $t_{\mathit{eff}}$ between neighboring rows is not limited to the interlace method exemplified in the eighth example, and the same effect can be obtained by another interlace method.

As described above, it is possible to perform the initializing operation RS and readout operation RO so as to produce a difference in time $t_{\mathit{eff}}$ between neighboring rows in the ninth example as well. Then, the correction information or correction coefficient can be calculated based on the difference in time $t_{\mathit{eff}}$ following the same procedures as in the eighth example. Accordingly, the same effects as those of the eighth example can be obtained by the ninth example as well.

Note that the interlace method for every three rows is exemplified in this example in order to simplify the explanation, but an interlace method for every four or more rows may also be used. In addition, X need not be a multiple of 3. Furthermore, other parameters are also not limited to the exemplified quantities.

(4-3. 10th Example)

In the above-described eighth and ninth examples, the modes in which the initializing operation RS and readout operation RO are performed by the interlace method so as to produce a difference in time $t_{\mathit{eff}}$ between neighboring rows is exemplified. However, the present invention is not limited to these modes.

Figure 23:
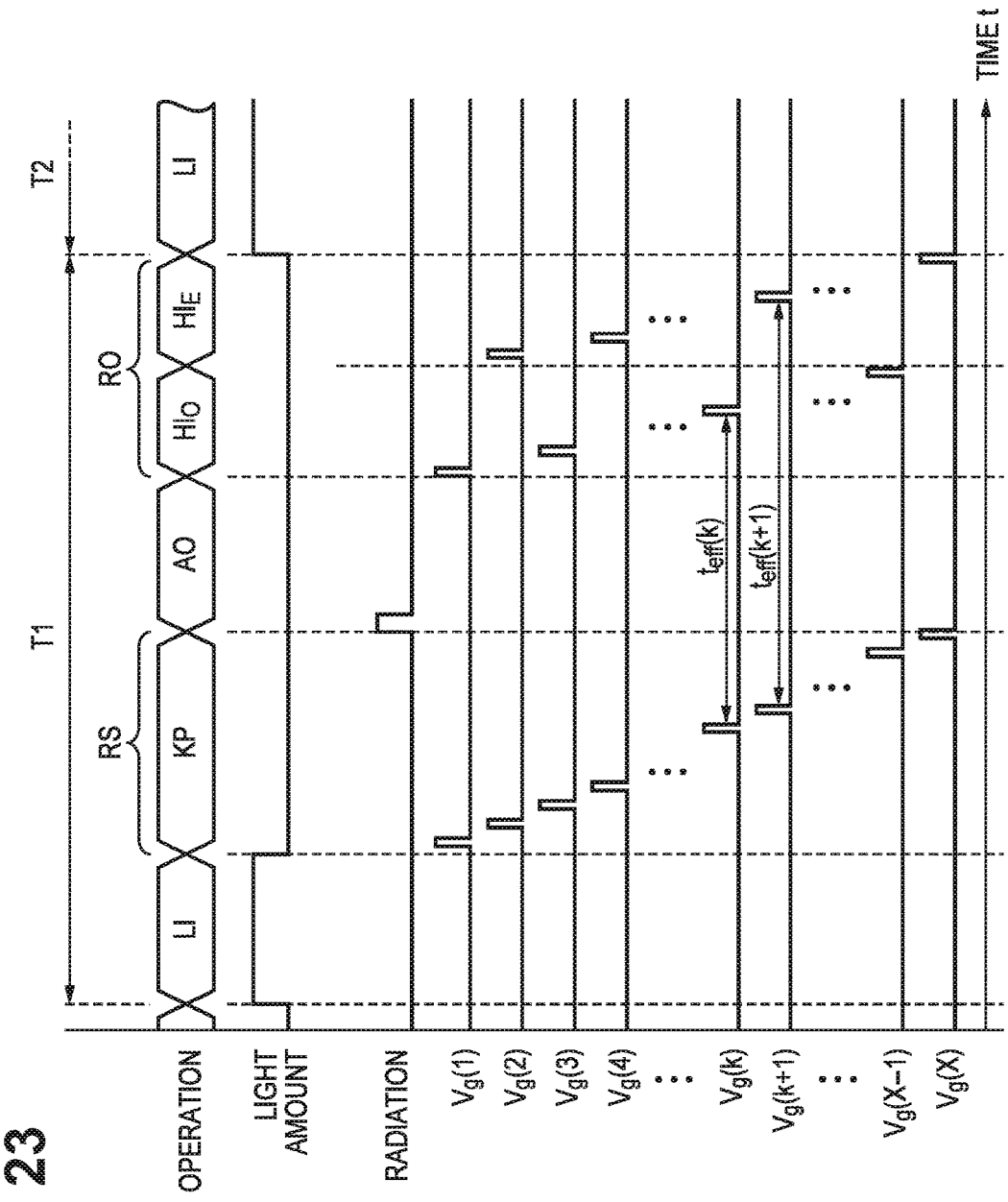
FIG. 23 is a timing chart for explaining an example of the operation of the radiation imaging apparatus.

FIG. 23 shows a driving timing chart of the 10th example in the same manner as the above-described eighth example (FIG. 20). The 10th example mainly differs from the eighth example in that the initializing operation RS is performed by the progressive method (the operation KP), and the readout operation RO is performed by the interlace method (the operations $HI_O$ and $HI_E$). Also, the 10th example mainly differs from the above-described ninth example in that the readout operation RO is performed without dividing the sensor array 110 into groups in the period T1, and the readout operation RO is performed by performing this division in the period T2.

FIG. 23 exemplifies a case in which the kth row is an odd-numbered row. When the kth row is an odd-numbered row, the following equations hold:

$$t_{\mathit{eff}}(k) = \{1 - (k-1)/2X\} \times t_R + t_{AO}$$

$$t_{\mathit{eff}}(k+1) = \{3/2 - k/2X\} \times t_R + t_{AO} \quad (313)$$

This produces a difference in time $t_{\mathit{eff}}$ between neighboring rows. Note that the case in which the kth row is an odd-numbered row is exemplified in this example, but it is possible to calculate the constant a and noise component N1 following the same procedures when the kth row is an even-numbered row.

As described above, the correction information or correction coefficient can be calculated based on the difference in time $t_{\mathit{eff}}$ in the 10th example as well. Accordingly, the same effects as those of the eighth embodiment and the like can be obtained by the 10th example as well.

Figure 24:
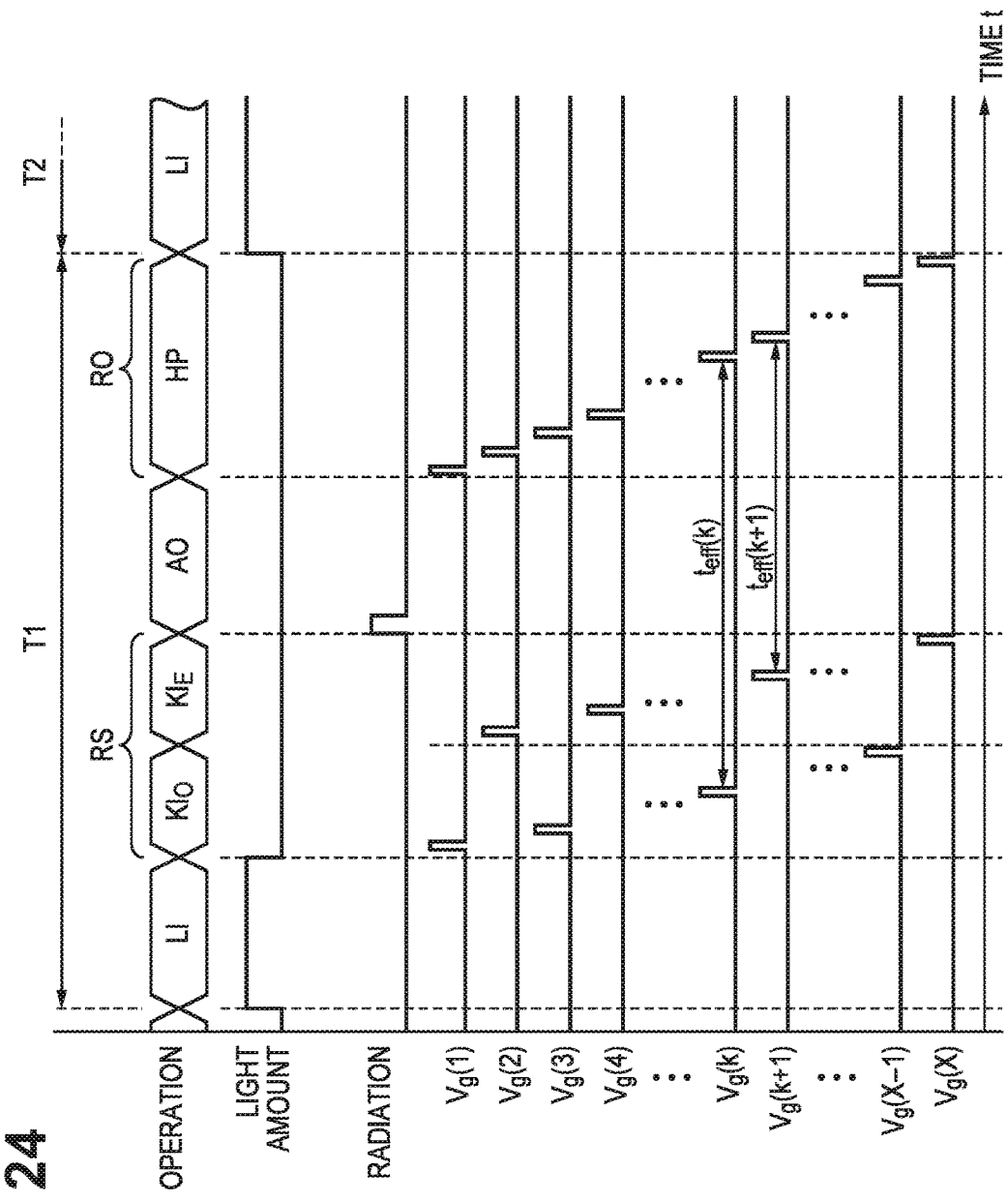
FIG. 24 is a timing chart for explaining an example of the operation of the radiation imaging apparatus.

Note that in the example shown in FIG. 23, the mode in which the progressive method (operation KP) is applied to the initializing operation RS and the interlace method (operations $HI_O$ and $HI_E$) is applied to the readout operation RO is exemplified. However, the opposite methods may also be applied to these operations. That is, as exemplarily shown in FIG. 24, it is also possible to apply the interface method (operations $KI_O$ and $KI_E$) to the initializing operation RS, and the progressive method (operation HP) to the readout operation RO. Thus, the driving method which produces a difference in time $t_{\mathit{eff}}$ between neighboring rows is not limited to the interlace method, and the same effects can be obtained by applying the interlace method to one of the initializing operation RS and readout operation RO, and the progressive method to the other.

Figure 25:
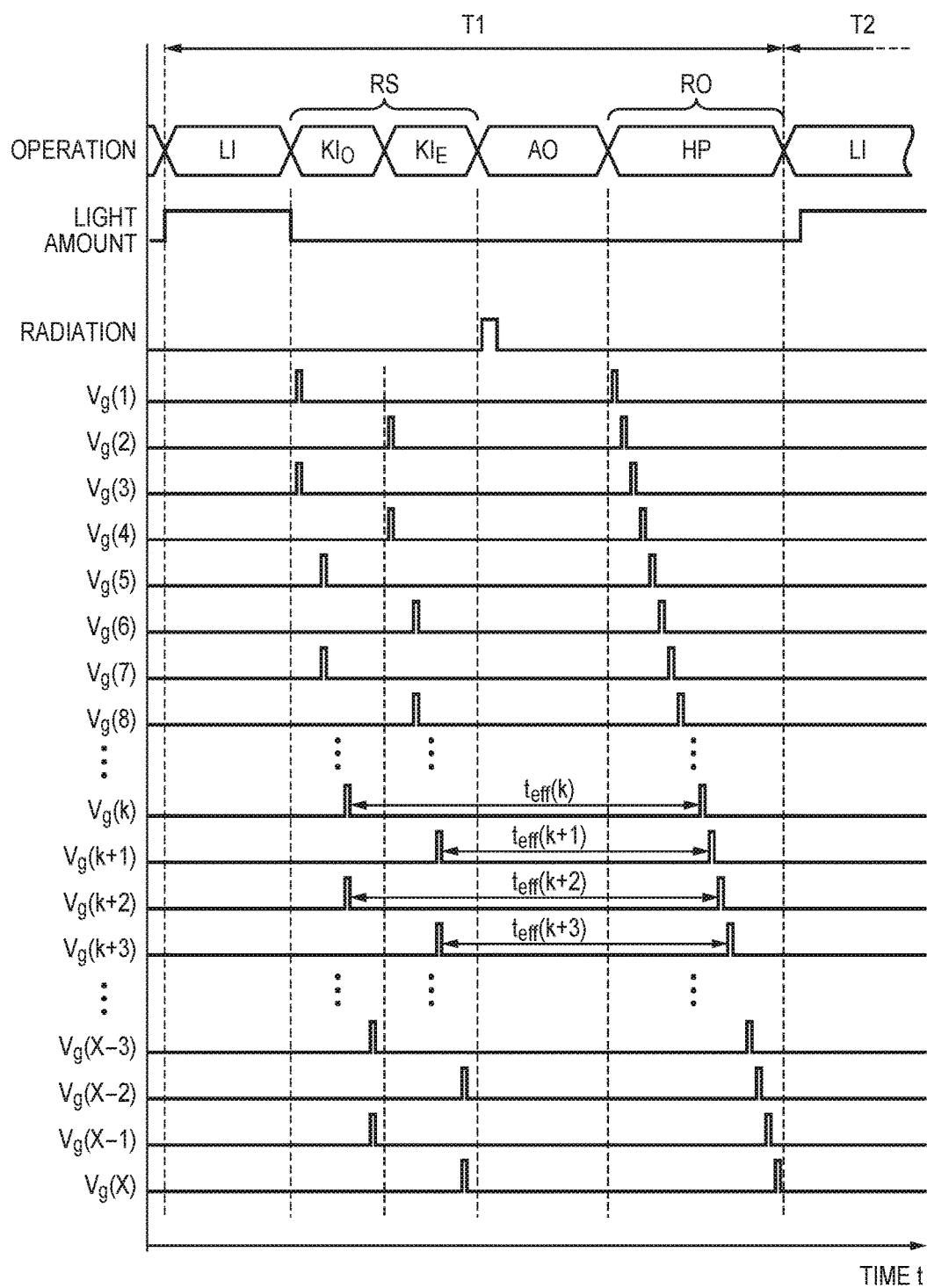
FIG. 25 is a timing chart for explaining an example of the operation of the radiation imaging apparatus.

Also, in the 10th example, the interlace method when the number of rows of the sensors S to be selected (at one time) is one is exemplified. As a modification, however, the number of rows to be selected may be two or more as exemplarily shown in FIG. 25. That is, in driving $KI_O$, the sensors S are initialized while sequentially selecting rows two by two, that is, the first and third rows, the fifth and seventh rows, . . . , the (X−3)th and (X−1)th rows. In driving $KI_E$, the sensors S are initialized while sequentially selecting rows two by two, that is, the second and fourth rows, the sixth and eighth rows, . . . , the (X−2)th and Xth rows. The opposite methods may also be applied to both the initializing operation RS and readout operation RO. In addition, the number of rows to be selected may also be three or more.

(4-4. 11th Example)

In the 11th example, correction for removing the noise component N2 is performed in addition to the above-described correction for removing the noise component N1. As described previously, the noise component N2 is a noise component having no dependence on time, for example, a noise component caused by FPN. This correction is performed based on image data obtained by a series of operations from an initializing operation ("RS2") to a readout operation ("RO2") which are performed in a state in which the apparatus IA is not irradiated, for example, before or after the start of irradiation. The series of operations are performed by the same driving method as described above, but in a state in which the apparatus IA is not irradiated.

Let $SS_1(m, n)$ be a signal obtained from the sensor $S(m, n)$ in the mth row and the nth column by the readout operation RO. In addition, let $S0_1(m, n), N1_1(m, n)$, and the like be corresponding components $S0, N1$, and the like. In this case, the signal $SS_1(m, n)$ can be represented by:

$$SS_1(m, n) = S0_1(m, n) + N1_1(m, n) + N2_1(m, n) \quad (314)$$
$$= a(m, n) \times \{t_1 e(m) - t_1 s(m)\} +$$
$$S0_1(m, n) + N2_1(m, n)$$

Also, let $SS_2(m, n)$ be a signal obtained from the sensor $S(m, n)$ in the mth row and the nth column by the readout operation RO2. In addition, let $S0_2(m, n), N1_2(m, n)$, and the like be corresponding components $S0, N1$, and the like. In this case, the signal $SS_2(m, n)$ can be represented by:

$$SS_2(m, n) = N1_2(m, n) + N2_2(m, n) \quad (315)$$
$$= a(m, n) \times \{t_2 e(m) - t_2 s(m)\} + N2_2(m, n)$$

A signal $SS_C(m, n)$ obtained by correcting the signal obtained by the readout operation RO based on the signal obtained by the readout operation RO2 can be represented by:

$$SS_C(m, n) \equiv SS_1(m, n) - SS_2(m, n) \quad (316)$$
$$= \{S0_1(m, n) + N1_1(m, n) + N2_1(m, n)\} -$$
$$\{N1_2(m, n) + N2_2(m, n)\}$$
$$= S0_1(m, n) + a(m, n) \times [\{t_1 e(m) - t_1 s(m)\} -$$
$$\{t_2 e(m) - t_2 s(m)\}]$$

In this case, the following expression holds:

$$N2_1(m, n) \approx N2_2(m, n) \quad (317)$$

After that, the above-described correction for removing the noise component N1 need only be performed on the corrected signal $SS_C(m, n)$ in the same manner as in each of the above-described examples.

That is, in the 11th example, correction for removing the noise component N2 is performed, and correction for removing the noise component N1 is performed on the image data obtained by the former correction by using the difference in time $t_{eff}$ between neighboring rows. The 11th example can achieve the same effects as those of the above-described eighth example, and can further remove the noise component N2 caused by FPN or the like.

(5. Others)

The several preferred embodiments and their examples have been described above, but the present invention is not limited to these embodiments and examples, and it is also possible to partially change the embodiments and examples and combine the embodiments and examples without departing from the spirit and scope of the invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A radiation imaging apparatus comprising:
a plurality of sensors arrayed to form a plurality of rows and a plurality of columns;
a driving unit configured to drive the plurality of sensors row by row; and
a correcting unit, wherein
a first irradiation is performed to the plurality of sensors, and then a second irradiation is performed to the plurality of sensors,
the driving unit performs,
    first driving to drive the plurality of sensors while selecting the plurality of rows in a first order, in accordance with the first irradiation, such that the plurality of sensors output signals corresponding to the first irradiation, and
    second driving to drive the plurality of sensors while selecting the plurality of rows in a second order, in accordance with the second irradiation, such that the plurality of sensors output signals corresponding to the second irradiation, the second order being different from the first order,
among two neighboring rows of the plurality of rows, (i) a period from when the sensor in one row is driven in the first driving to when the sensor in the one row is driven in the second driving and (ii) a period from when the sensor in the other row is driven in the first driving to when the sensor in the other row is driven in the second driving are different from each other, and
the correcting unit corrects a signal from the sensor driven in the second driving in at least one of a first row and a second row neighboring each other, based on a signal from the sensor in the first row, a signal from the sensor in the second row and a difference of the period between the first row and the second row.

2. The apparatus according to claim 1, further comprising a divider configured to divide the plurality of sensors into two or more groups row by row, wherein the divider divides the plurality of sensors such that two neighboring rows belong to two different groups, respectively, and the driving unit performs the first driving and the second driving group by group.

3. The apparatus according to claim 2, wherein the number of groups divided by the divider is two, and the driving unit performs the first driving and the second driving by an interlace method.

4. The apparatus according to claim 1, further comprising a divider configured to divide the plurality of sensors into two or more groups row by row, wherein the divider divides the plurality of sensors such that two neighboring rows belong to two different groups, respectively, and the driving unit performs one of the first driving and the second driving group by group.

5. The apparatus according to claim 1, further comprising a calculating unit configured to calculate correcting information for correcting the signal from the sensor in the at least one of the first row and the second row, based on the signal from the sensor in the first row, the signal from the sensor in the second row and the difference of the period between the first row and the second row, wherein the correcting unit corrects the signal from the sensor in the at least one of the first row and the second row, based on the correcting information calculated by the calculating unit.

6. The apparatus according to claim 5, wherein the calculating unit calculates the correcting information, based on a difference between the signal from the sensor in the first row and the signal from the sensor in the second row, and the difference of the period between the first row and the second row.

7. The apparatus according to claim 5, wherein the plurality of sensors are divided into two or more regions, and the calculating unit calculates the correcting information for each region.

8. The apparatus according to claim 7, wherein the plurality of sensors are divided into two or more regions for at least every two rows, for at least every two columns, or for every unit region including at least two rows and at least two columns.

9. The apparatus according to claim 5, further comprising a determination unit configured to determine whether the correcting information satisfies a predetermined condition, wherein the correcting unit does not correct the signal from the sensor in the at least one of the first row and the second row, in a case where the determination unit does not determine the correcting information satisfies the predetermined condition.

10. The apparatus according to claim 5, wherein the driving unit drives the plurality of sensors, before/after both the first irradiation and the second irradiation, to output signals corresponding to charges generated in the plurality of sensors in a state of non-irradiation, and the correcting unit performs first correction to correct signals from the plurality of sensors driven in the second driving, using signals from the plurality of sensors in the state of non-irradiation, and second correction to correct the signal from the sensor in the at least one of the first row and the second row, among the signals corrected in the first correction, using the signal from the sensor the first row, the signal from the sensor the second row, and the difference of the period between the first row and the second row.

11. The apparatus according to claim 1, wherein the signal from each sensor driven in the second driving includes a noise component corresponding to the period from when the sensor is driven in the first driving to when the sensor is driven in the second driving.

12. The apparatus according to claim 1, further comprising a measurement unit configured to measure the period for the sensor in each row.

13. The apparatus according to claim 1, further comprising a radiation generation source configured to generate radiation.

14. A method for controlling a radiation imaging apparatus, the apparatus comprising a plurality of sensors arrayed to form a plurality of rows and a plurality of columns, and a driving unit configured to drive the plurality of sensors row by row, the method comprising:

first driving to drive the plurality of sensors while selecting the plurality of rows in a first order, in accordance with the first irradiation, such that the plurality of sensors output signals corresponding to the first irradiation;

second driving to drive the plurality of sensors while selecting the plurality of rows in a second order, in accordance with the second irradiation, such that the plurality of sensors output signals corresponding to the second irradiation, the second order being different from the first order; and correcting a signal, wherein, among two neighboring rows of the plurality of rows, (i) a period from when the sensor in one row is driven in the first driving to when the sensor in the one row is driven in the second driving and (ii) a period from when the sensor in the other row is driven in the first driving to when the sensor in the other row is driven in the second driving are different from each other, and in the correcting, a signal from the sensor driven in the second driving in at least one of a first row and a second row neighboring each other is corrected, based on a signal from the sensor in the first row, a signal from the sensor in the second row and a difference of the period between the first row and the second row.

* * * * *